United States Patent
Hurst

(10) Patent No.: US 11,974,810 B2
(45) Date of Patent: May 7, 2024

(54) OPHTHALMIC IMAGING SYSTEM

(71) Applicant: Optos Plc, Dunfermline (GB)

(72) Inventor: Daniel Hurst, Dunfermline (GB)

(73) Assignee: Optos Plc, Dunfermline (GB)

(*) Notice: Subject to any disclaimer, the term of this patent is extended or adjusted under 35 U.S.C. 154(b) by 664 days.

(21) Appl. No.: 17/036,184

(22) Filed: Sep. 29, 2020

(65) Prior Publication Data
US 2021/0100448 A1  Apr. 8, 2021

(30) Foreign Application Priority Data
Oct. 7, 2019  (EP) .................................... 19201717

(51) Int. Cl.
| | |
|---|---|
| *A61B 3/10* | (2006.01) |
| *A61B 3/02* | (2006.01) |
| *A61B 3/12* | (2006.01) |
| *A61B 3/14* | (2006.01) |
| *G06T 5/00* | (2006.01) |
| *G06T 5/50* | (2006.01) |

(52) U.S. Cl.
CPC .................. *A61B 3/12* (2013.01); *A61B 3/14* (2013.01); *G06T 5/002* (2013.01); *G06T 5/50* (2013.01); *G06T 2207/20221* (2013.01); *G06T 2207/30041* (2013.01)

(58) Field of Classification Search
CPC ......... A61B 3/02; A61B 3/102; A61B 3/1025; A61B 3/1015; A61B 3/1225; A61B 3/024
USPC ........ 351/206, 200, 205, 210, 221–223, 246
See application file for complete search history.

(56) References Cited

U.S. PATENT DOCUMENTS 5,815,242 A    9/1998  Anderson et al.
8,325,996 B2*  12/2012  Martin .................. G06V 40/193
                                                           382/206
(Continued)

FOREIGN PATENT DOCUMENTS

| EP | 3449806 A1 | 3/2019 |
|---|---|---|
| JP | 2006-333902 | 12/2006 |

(Continued)

OTHER PUBLICATIONS

European Search Report dated Jun. 18, 2020 in European patent application No. 19201717.06-1122.
(Continued)

*Primary Examiner* — Dawayne Pinkney
(74) *Attorney, Agent, or Firm* — FAEGRE DRINKER BIDDLE & REATH

(57) ABSTRACT

An imaging system for generating an image of a region of an eye, comprising: an ocular imaging device controlled by a control module to acquire, from a first viewpoint, a first ocular image of the region having an image artefact caused by obstruction from imaging of a part of the region by an object, and a second ocular image from a predetermined second viewpoint, which shows at least a portion of the part of the region that was obstructed from imaging during acquisition of the first ocular image; and an image data processing module for combining the first and second ocular images to generate an enhanced ocular image having an image artefact caused by obstruction from imaging by the object which is smaller in relation to the image artefact in the first or second ocular image, or no such image artefact.

20 Claims, 19 Drawing Sheets

(56) References Cited

U.S. PATENT DOCUMENTS

| | | | |
|---|---|---|---|
| 10,852,817 B1* | 12/2020 | Ouderkirk | G06V 40/18 |
| 2009/0180073 A1 | 7/2009 | Ichikawa et al. | |
| 2011/0234977 A1 | 9/2011 | Verdooner | |
| 2014/0063465 A1 | 3/2014 | Numajiri | |

FOREIGN PATENT DOCUMENTS

| | | |
|---|---|---|
| JP | 2009-15518 | 1/2009 |
| JP | 2013-527775 | 7/2013 |
| WO | WO2015039102 A1 | 3/2015 |
| WO | WO2017034861 A1 | 3/2017 |
| WO | 2019-036196 | 2/2019 |

OTHER PUBLICATIONS

Notice of Reasons for Rejection dated Nov. 9, 2021 (2 sheets) in Japanese patent application No. 2020-170096; (Enhlish translation attached—3 sheets).

* cited by examiner

|  | $\varphi = 10$ | $\varphi = 20$ | $\varphi = 30$ | $\varphi = 40$ |
|---|---|---|---|---|
| $\theta = 10$ | v1 | v2 | v3 | v4 |
| $\theta = 20$ | v5 | v6 | v7 | v8 |
| $\theta = 30$ | v9 | v10 | v11 | v12 |
| $\theta = 40$ | v13 | v14 | v15 | v16 |

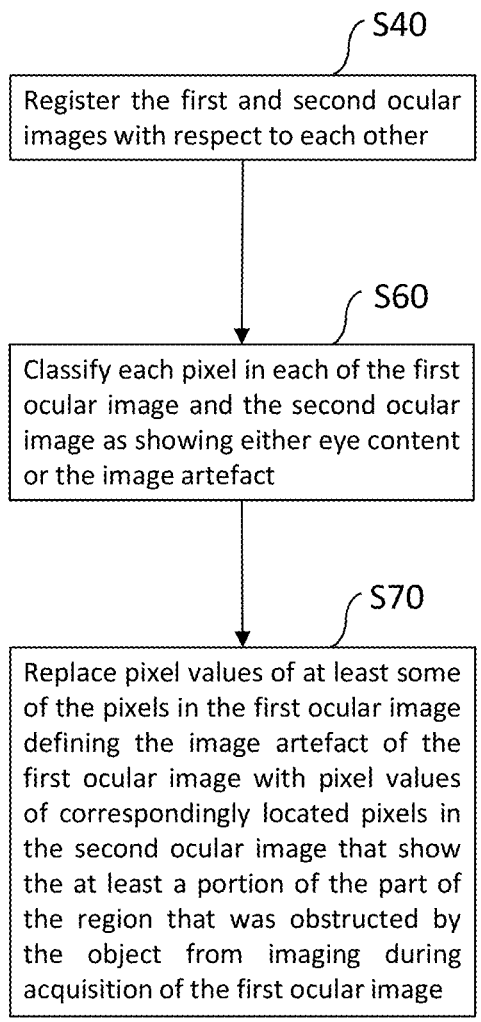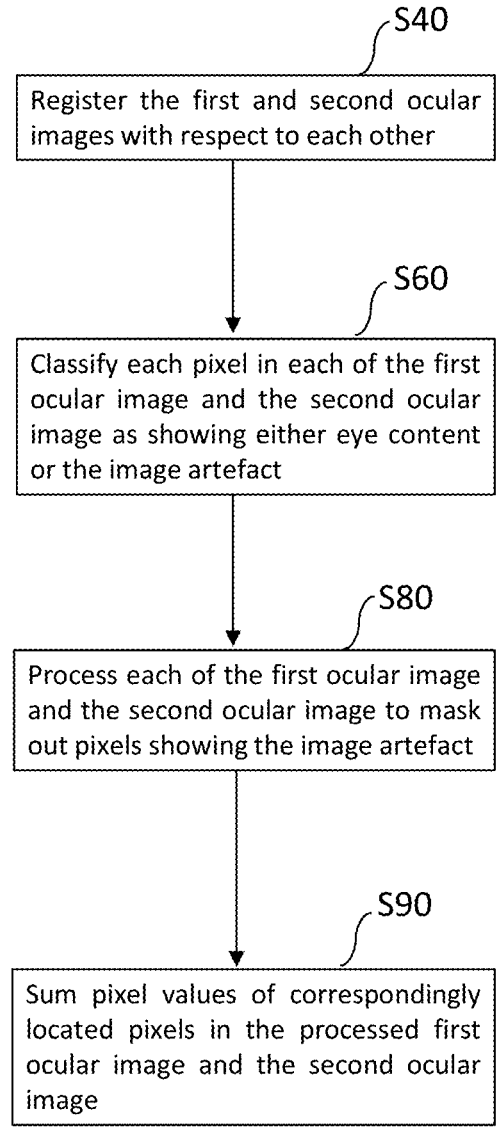
Fig. 11
Fig. 12

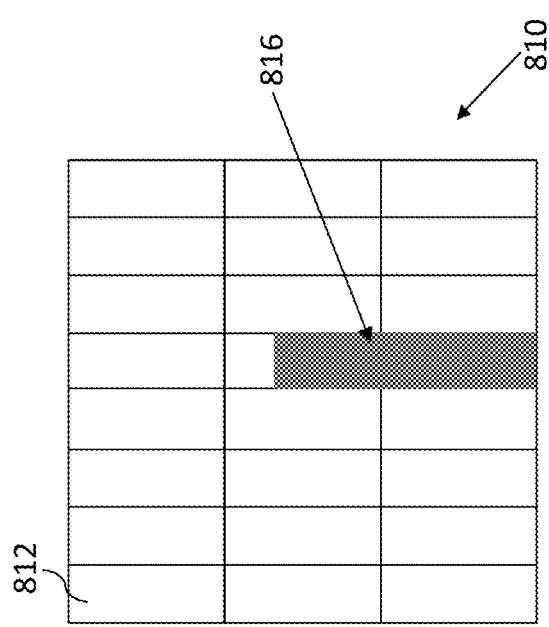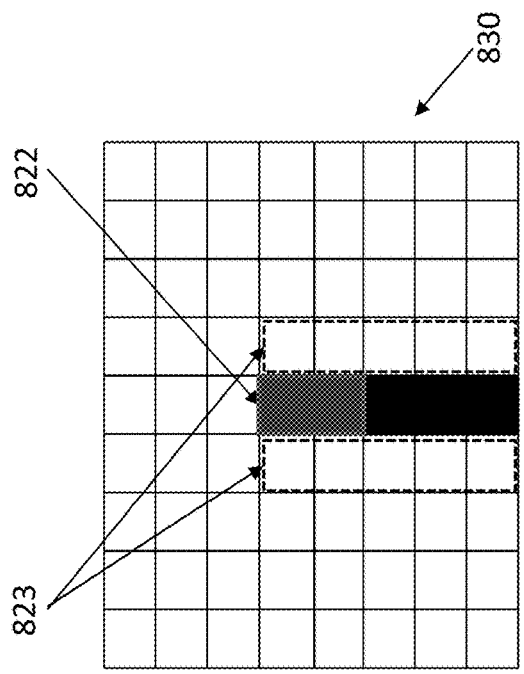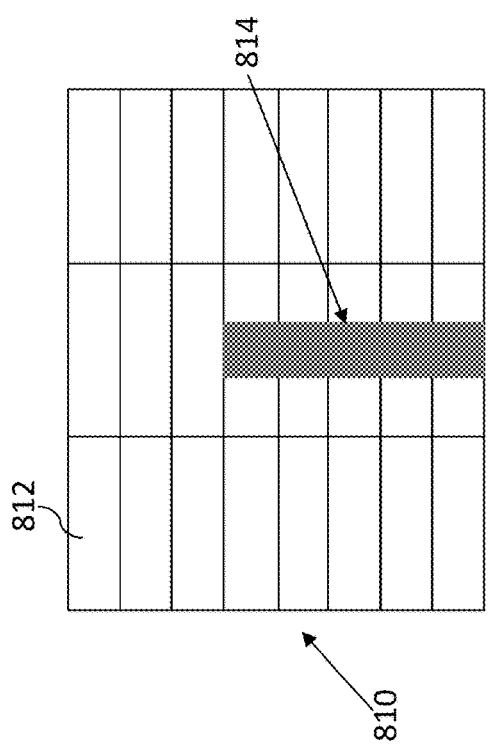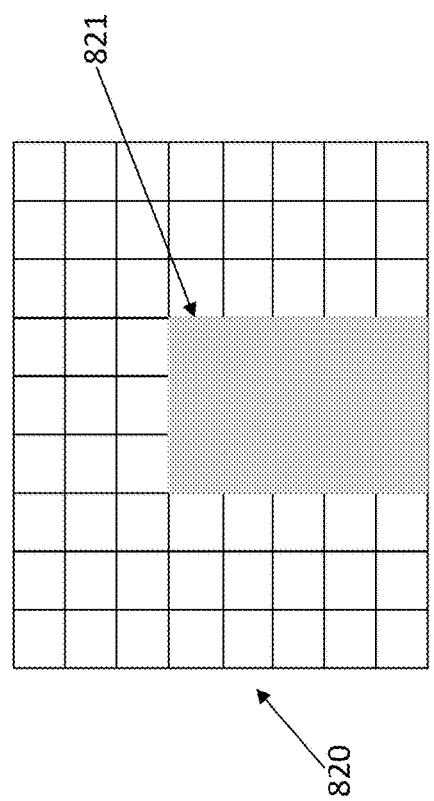

OPHTHALMIC IMAGING SYSTEM

CROSS REFERENCE TO RELATED APPLICATION

This application claims the benefit of priority based on European Patent Application EP 19 201 717.6 filed Oct. 7, 2019, the entirety of which is incorporated by reference as if set forth fully herein.

TECHNICAL FIELD

Example aspects herein generally relate to the field of ophthalmic imaging systems for acquiring images of an eye of a subject and, more particularly, to a technique for generating an enhanced image of the eye by combining the acquired images.

BACKGROUND

In the field of ocular imaging, it is known to combine images of a common region of the eye (e.g. the retina) using pixel averaging, for example, in order to improve image quality by increasing the signal-to-noise ratio. This approach has been used in many different applications. For example, some ophthalmic devices combine scanning laser ophthalmoscope (SLO) functionality with optical coherence tomography (OCT) functionality to acquire two-dimensional SLO images of the retinal surface and, concurrently, tomographic data for generating a three-dimensional image of the retina beneath the retinal surface. In such combined SLO/OCT imaging systems, high frame-rate SLO images have been used to track eye movements, with the acquired eye-tracking information being used to stabilise the OCT scan location. By averaging multiple SLO images, the quality of image registration and eye tracking can be improved, allowing high-quality OCT scans of a targeted region of interest to be acquired.

SUMMARY

There is provided, in accordance with a first example aspect herein, an ophthalmic imaging system for generating an image of a region of an eye of a subject. The ophthalmic imaging system comprises an ocular imaging device operable to acquire an ocular image of the region. The ophthalmic imaging system further comprises a control module configured to control the ocular imaging device to acquire, from a first viewpoint relative to the region, a first ocular image of the region having an image artefact caused by obstruction from imaging of a part of the region by an object between the ocular imaging device and the region during acquisition of the first ocular image. The control module is further configured to control the ocular imaging device to acquire a second ocular image from a predetermined second viewpoint that is different from the first viewpoint, the second ocular image showing at least a portion of the part of the region that was obstructed by the object from imaging during acquisition of the first ocular image. The ophthalmic imaging system further comprises an image data processing module configured to combine image data of the first ocular image with image data of the second ocular image to generate an enhanced ocular image. The enhanced ocular image either has no image artefact caused by obstruction from imaging of a part of the region by the object between the ocular imaging device and the region during acquisition of the first ocular image or the second ocular image, or an image artefact that is based on at least one of the image artefact in the first ocular image or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

There is provided, in accordance with a second example aspect herein, an ophthalmic imaging system for generating an image of a region of an eye of a subject. The ophthalmic imaging system comprises an ocular imaging device having a two-dimensional array of photodetector elements and operable to acquire an ocular image of the region from a viewpoint. Each photodetector element of the photodetector elements has at least one of: a first length along a first array direction of the two-dimensional array that differs from a second length along a second array direction of the two-dimensional array; or a first separation from a first adjacent photodetector element which is adjacent in the first array direction, the first separation being different from a second separation of the photodetector element from a second adjacent photodetector element which is adjacent in the second array direction. The ophthalmic imaging system further comprises a rotation mechanism configured to rotate the ocular imaging device about a rotation axis passing through the eye and the viewpoint; and a control module configured to: control the ocular imaging device to acquire, from the viewpoint, a first ocular image of the region having an image artefact caused by obstruction from imaging of a part of the region by an object between the ocular imaging device and the region during acquisition of the first ocular image; control the rotation mechanism to rotate the ocular imaging device about the rotation axis; and, following the rotation of the ocular imaging device, control the ocular imaging device to acquire a second ocular image from the viewpoint, the second ocular image showing at least a portion of the part of the region that was obstructed by the object from being imaged during acquisition of the first ocular image. The ophthalmic imaging system further comprises an image data processing module configured to combine image data of the first ocular image with image data of the second ocular image to generate an enhanced ocular image having one of: no image artefact caused by obstruction from imaging of a part of the region by the object between the ocular imaging device and the region during acquisition of the first ocular image or the second ocular image; or an image artefact that is based on at least one of the image artefact in the first ocular image, or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

There is provided, in accordance with a third example aspect herein, a computer program comprising instructions which, when the computer program is executed by a processor, cause the processor to control an ophthalmic imaging system comprising an ocular imaging device which is operable to acquire an image of a region of an eye of a subject. The instructions, when the computer program is executed by a processor, cause the processor to control the ophthalmic imaging system by: controlling the ocular imaging device to acquire, from a first viewpoint relative to the region, a first ocular image of the region having an image artefact caused by obstruction from imaging of a part of the region by an object between the ocular imaging device and the region during acquisition of the first ocular image; controlling the ocular imaging device to acquire a second ocular image from a predetermined second viewpoint that is different from the first viewpoint, the second ocular image showing at least a portion of the part of the region that was obstructed by the object from being imaged during acquisition of the first ocular image; and combining image data of the first ocular image with image data of the second ocular image to generate an enhanced ocular image having one of: no image artefact caused by obstruction from imaging of a part of the region by the object between the ocular imaging device and the region during acquisition of the first ocular image or the second ocular image; or an image artefact that is based on at least one of the image artefact in the first ocular image or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

Furthermore, there is also provided, in accordance with a fourth example aspect herein, a computer program comprising instructions which, when the computer program is executed by a processor, cause the processor to control an ophthalmic imaging system comprising: an ocular imaging device comprising a two-dimensional array of photodetector elements and operable to acquire an ocular image of the region from a viewpoint, wherein each photodetector element of the photodetector elements has at least one of: a first length along a first array direction of the two-dimensional array that differs from a second length along a second array direction of the two-dimensional array; or a first separation from a first adjacent photodetector element which is adjacent in the first array direction, the first separation being different from a second separation of the photodetector element from a second adjacent photodetector element which is adjacent in the second array direction. The ophthalmic imaging system further comprises a rotation mechanism configured to rotate the ocular imaging device about a rotation axis passing through the eye and the viewpoint. The instructions, when the computer program is executed by a processor, cause the processor to control the ophthalmic imaging system by: controlling the ocular imaging device to acquire, from the viewpoint, a first ocular image of the region having an image artefact caused by obstruction from imaging of a part of the region by an object between the ocular imaging device and the region during acquisition of the first ocular image; controlling the rotation mechanism to rotate the ocular imaging device about the rotation axis; and, following the rotation of the ocular imaging device, controlling the ocular imaging device to acquire a second ocular image from the viewpoint, the second ocular image showing at least a portion of the part of the region that was obstructed by the object from being imaged during acquisition of the first ocular image. The instructions, when the computer program is executed by a processor, further cause the processor to: combine image data of the first ocular image with image data of the second ocular image to generate an enhanced ocular image having one of: no image artefact caused by obstruction from imaging of a part of the region by the object between the ocular imaging device and the region during acquisition of the first ocular image or the second ocular image; or an image artefact that is based on at least one of the image artefact in the first ocular image or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

FIG. 11 illustrates an alternative method of generating an enhanced ocular image with a reduced image artefact, in another example embodiment herein.

FIG. 12 illustrates a further alternative method of generating an enhanced image with a reduced image artefact, in another example embodiment herein.

FIG. 21A illustrates an illumination of the photodetector array of the ophthalmic imaging device according to the sixth example embodiment with an illumination pattern comprising a shadow which obscures part of the photodetector array.

FIG. 21B illustrates a first ocular image acquired by the ocular imaging device based on light detected by the photodetector array thereof when the photodetector array has been illuminated with an illumination pattern as illustrated in FIG. 21A.

FIG. 21C illustrates an illumination of the photodetector array of the ophthalmic imaging device according to the sixth example embodiment, after it has been rotated clockwise by 90 degrees, with the same illumination pattern as in the example of FIG. 21A.

FIG. 21D illustrates a second ocular image acquired by the ocular imaging device based on light detected by the photodetector array thereof when the photodetector array has been rotated and illuminated with an illumination pattern as illustrated in FIG. 21C.

DETAILED DESCRIPTION OF EXAMPLE EMBODIMENTS

During imaging of a region of the eye, such as the retina or an anterior part of the eye, for example, an intervening object (e.g. an eyelash, an iris or an eyelid of the eye, or a hair from the subject's head) located between the eye and the imaging device can lead to a reduction in the amount of useful information obtained from the imaging process. For instance, eyelashes may prevent an incident scanning beam from a scanning laser ophthalmoscope or other kind of eye scanner from propagating to a target region on the retina of the eye, causing unwanted image artefacts in the form of "eyelash shadows" to appear in the acquired image of the eye. During a typical SLO retinal scan, eyelashes obscure approximately one third of the image field of view, and can significantly reduce the amount of retinal content in the acquired image. Similar problems arise in other types of ocular imaging. For example, when photographing an anterior segment of the eye, images of eyelashes may be overlaid on acquired image of the anterior segment of the eye, resulting in reduced visibility of the anterior segment itself.

The techniques of acquiring ocular images and combining the acquired ocular images described herein can advantageously allow an enhanced ocular image to be created, in which image artefacts of the kind described above are reduced or eliminated altogether, allowing more of the imaged region of the eye to be visible in the image. As will be explained in more detail below, images of the eye are acquired by an ocular imaging device from different vantage points (i.e. viewpoints or perspectives), such that the parallax effect causes an image artefact of an eyelash or other intervening object to appear at different respective locations in the acquired images. These ocular images are then combined to generate an enhanced ocular image in such a way that their non-artefact related image contents complement one another, with the image artefact in the enhanced ocular image being reduced (in spatial extend and/or average pixel intensity, for example) relative to the artefacts in the acquired images, or eliminated altogether. The ophthalmic imaging system of an example embodiment herein is effectively able to 'look around' the object in a controlled way, from two or more viewpoints, and thus image more of the targeted part of the eye than could be achieved from a single viewpoint.

The enhanced ocular images thus generated can be used in a variety of applications. For example, improving the SLO images acquired by a combined SLO/OCT imaging system in this way may improve the reliability of SLO image registration and the eye tracking described above, allowing the imaging region of the OCT scanner of the combined SLO/OCT imaging system to be more accurately maintained at a desired target location and thus an improved OCT image to be produced.

Example embodiments will now be explained in detail, with reference to the accompanying drawings.

Example Embodiment 1

Figure 1:
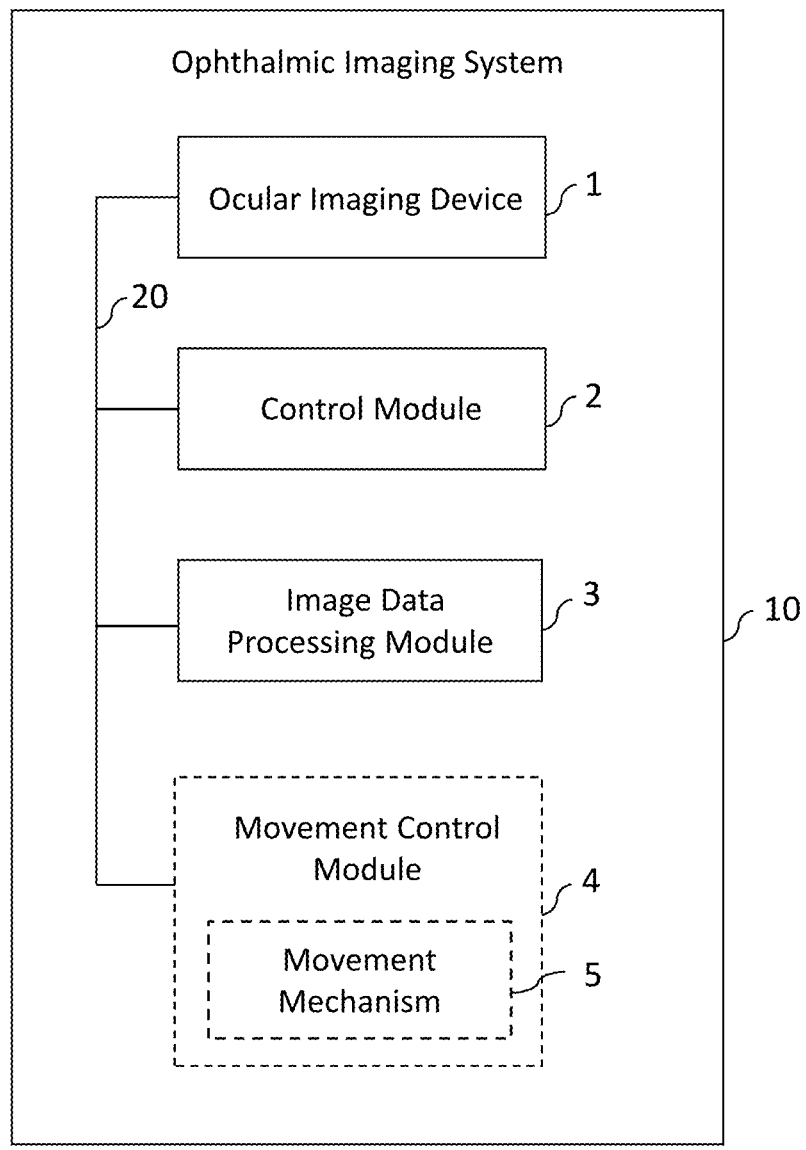
FIG. 1 is a schematic illustration of an ophthalmic imaging system according to a first example embodiment herein.
Figure 2:
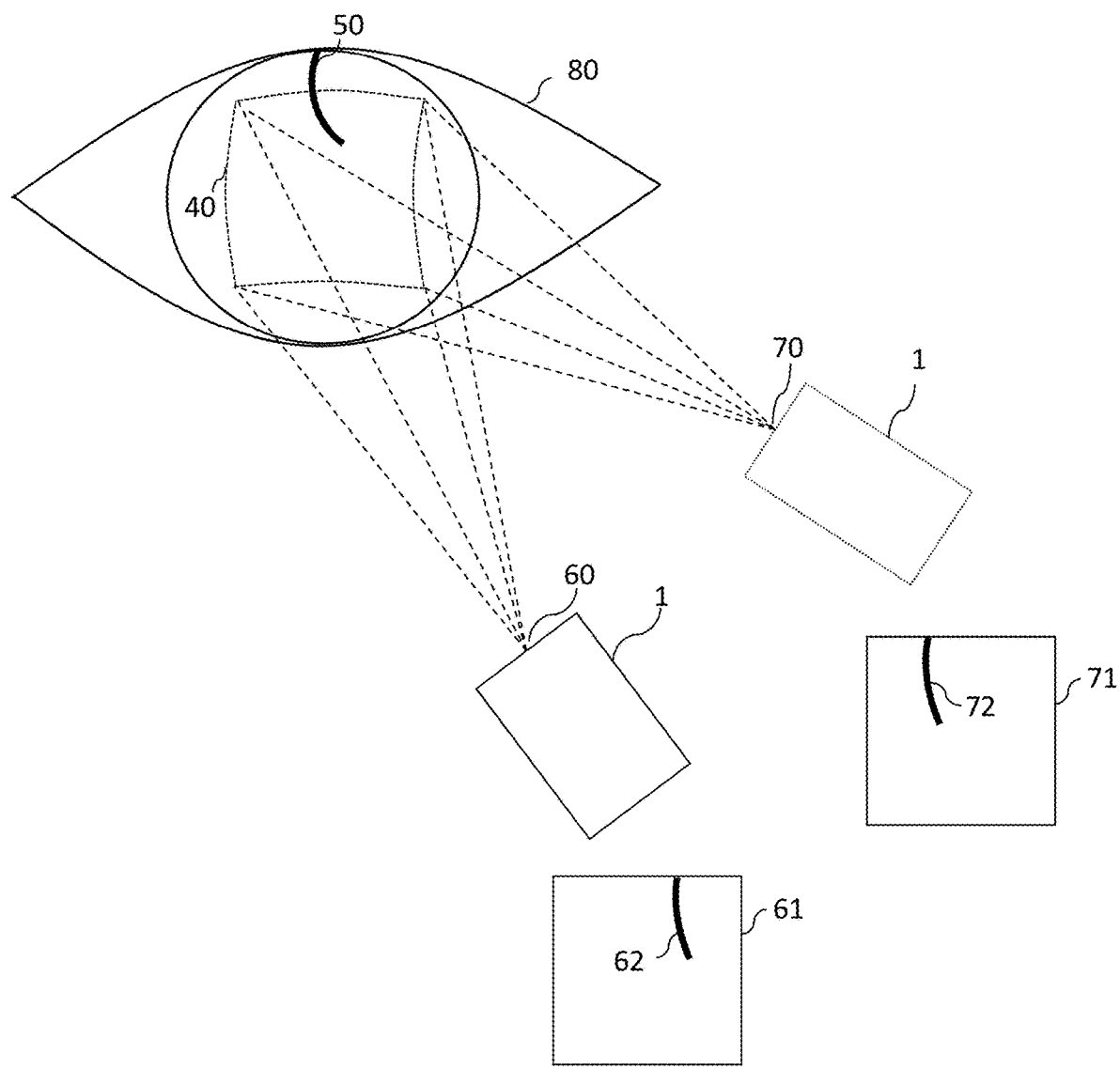
FIG. 2 illustrates two different viewpoints for performing eye imaging, and schematics of the respective ocular images captured from the two viewpoints, according to an example embodiment.

FIG. 1 is a schematic illustration of an ophthalmic imaging system 10 according to a first example embodiment herein, comprising an ocular imaging device 1, a control module 2 and an image data processing module 3. The ophthalmic imaging system 10 may, as in the present example embodiment, further comprise a movement control module 4. Referring to FIG. 2, the ocular imaging device 1 of the ophthalmic imaging system 10 is operable to capture a first ocular image 61 of a region 40 of an eye 80 from a first viewpoint 60, and a second ocular image 71 from a second, different viewpoint 70.

The ocular imaging device 1 may, as in the present example embodiment, take the form of an SLO. However, the ocular imaging device 1 is not limited to an SLO, and may alternatively take the form of any other type of ocular imaging device, such an eye camera, which may be configured for photographing the retina or an anterior segment of the eye 80. In the present example embodiment, the region 40 of the eye 80 imaged by the ocular imaging device 1 is a part of the retina, although in other embodiments, the region 40 could alternatively be another part of the eye 80 such as, for example, the cornea or another structure in the anterior segment of the eye. As details of the SLO and other commonplace ocular imaging systems are well-known to those skilled in the art, they will not be described further here.

Referring to FIG. 2, the control module 2 is configured to control the ocular imaging device 1 to acquire, from the first viewpoint 60 relative to the region 40, the first ocular image 61 of the region 40 having an image artefact 62 caused by obstruction from imaging of a part of the region 40 by an object 50 which is located between the ocular imaging device 1 and the region 40 during acquisition of the first ocular image 61. The object 50 may be any object which is located between the eye 80 and the ocular imaging device 1, and which prevents the ocular imaging device 1 from imaging a part of the region 40 of the eye 80 that is obscured from view by the object. In the present example, the object 50 takes the form of an eyelash, although it could alternatively be a hair from the head of the subject, for example.

The second ocular image 71, which is acquired by the ocular imaging device 1 from the predetermined second viewpoint 70, shows at least a portion of the part of the region 40 that was obstructed by the object 50 from imaging during acquisition of the first ocular image 61. As illustrated in FIG. 2, the first viewpoint 60 and the predetermined second viewpoint 70 may be arranged such that the region 40 of the eye 80 is imaged from different directions. It should be noted, however, that the first and second viewpoints, 60 and 70, could alternatively be arranged such that the region 40 of the eye 80 is imaged from a common direction, with one of the viewpoints being closer to the region 40 than the other view point. In this latter case, the size of the region 40 that is obscured from imaging by the object 50 is dependent on the distance of the viewpoint from the region 40, as the proportion of the ocular imaging device's field-of-view that is filled by the object 50 increases as the distance of the viewpoint to the region 40 decreases.

The image data processing module 3 is configured to combine image data of the first ocular image 61 with image data of the second ocular image 71 to generate an enhanced ocular image. The enhanced ocular image may have no image artefact caused by obstruction from imaging of a part of the region 40 of the eye 80 by the object 50 during acquisition of the first ocular image 61 or the second ocular image 71. Alternatively, the enhanced ocular image may have an image artefact that is based on at least one of the image artefact in the first ocular image 61 or an image artefact in the second ocular image 71 caused by obstruction from imaging of a part of the region 40 by the object 50 between the ocular imaging device 1 and the region 40 during acquisition of the second ocular image 71. In such case, the image artefact of the enhanced ocular image would be smaller, e.g. in its spatial extent and/or its average pixel intensity, in relation to at least one of the image artefact in the first ocular image 61 or the image artefact in the second ocular image 71.

The (optional) movement control module 4 is operable to control a movement of the viewpoint of the ocular imaging device 1 with respect to the region 40 of the eye 80. The control module 2 is configured to control the movement control module 4 to cause a predetermined movement of the viewpoint of the ocular imaging device 1 with respect to the region 40 of the eye 80 following the acquisition of the first ocular image 61, such that the ocular imaging device 1 is, following the movement, arranged to acquire the second ocular image 71 from the predetermined second viewpoint 70. Following the predetermined movement, the control module 2 is further configured to control the ocular imaging device 1 to acquire the second ocular image 71 from the predetermined second viewpoint 70.

The movement control module 4 may, as in the present example embodiment, comprise a movement mechanism 5, which is operable to make a predetermined movement of the viewpoint of the ocular imaging device 1 with respect to the region 40 by moving the viewpoint of the ocular imaging device 1 with respect to the region 40 in a direction along at least one of three different movement axes. The movement axes may, as in the present example embodiment, be orthogonal but the movement axes are not so limited.

However, in other example embodiments, the movement mechanism may instead be operable to move the viewpoint of the ocular imaging device 1 with respect to the region 40 by rotating the viewpoint of the ocular imaging device 1 about at least one of three different axes of rotation. The axes of rotation may extend in any direction, and may or may not pass through the eye 80 of the subject. Thus, the viewpoint of the ocular imaging device 1 may move along an arc of a circle instead of moving along a straight line. The movement mechanism may more generally move the viewpoint of the ocular imaging device 1 along any path from the first viewpoint 60 to the second viewpoint 70.

The control module 2 is further configured to cause the movement control module 4 to control the movement mechanism 5 so as to make the predetermined movement.

The ocular imaging device 1, the control module 2, the image data processing module 3 and the movement control module 4 are connected to one another by any appropriate communication connection, such as a bus 20, which allows various information to be exchanged between these modules.

The ophthalmic imaging system 10 is able to suppress the appearance of image artefacts caused by an object 50 in the field of view of the ocular imaging device 1 by imaging the eye 80 from a number of different predetermined viewpoints to acquire images from the respective different viewpoints, and combining the images from the different perspectives to produce an enhanced image in which the appearance of image artefacts caused by the object 50 is removed or reduced.

Figure 3:
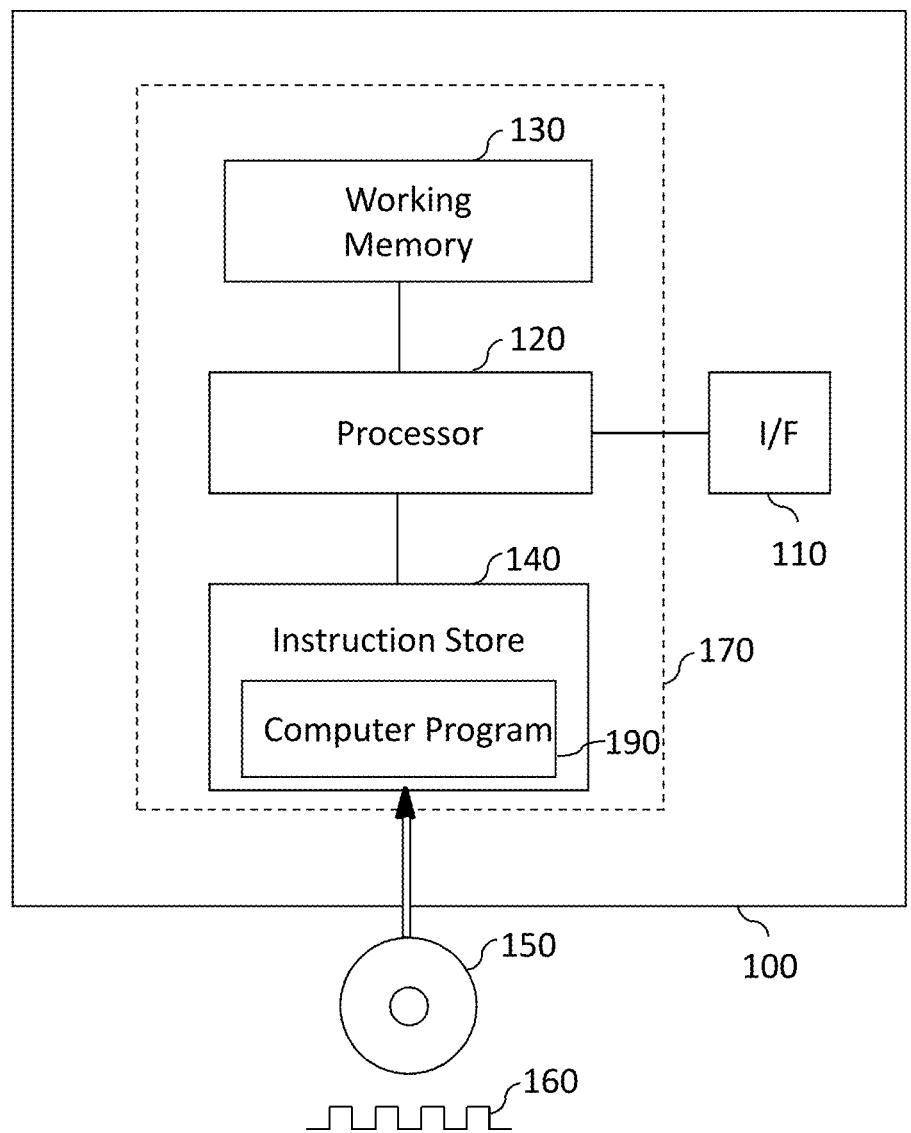
FIG. 3 shows an example of a hardware implementation of a control module and an image data processing module as shown in FIG. 1.

FIG. 3 shows an exemplary implementation of the control module 2 and the image data processing module 3 of FIG. 1, in programmable signal processing hardware. The signal processing apparatus shown in FIG. 3 comprises a communication interface (I/F) 110 for transmitting, via the bus 20, control signals to the ocular imaging device 1 and the movement control module 4, as well as receiving acquired image data from ocular imaging device 1. The signal processing apparatus 100 further comprises a processor (CPU) 120 for controlling the overall operation of the ophthalmic imaging system 10, a working memory 130 (e.g. a random access memory) and an instruction store 140 storing a computer program 190 comprising computer-readable instructions which, when executed by the processor 120, cause the processor 120 to perform the processing operations hereinafter described to control the ophthalmic imaging system 10. The instruction store 140 may comprise a ROM (e.g. in the form of an electrically-erasable programmable read-only memory (EEPROM) or flash memory) which is pre-loaded with the computer-readable instructions. Alternatively, the instruction store 140 may comprise a RAM or similar type of memory, and the computer-readable instructions can be input thereto from a computer program product, such as a computer-readable storage medium 150 such as a CD-ROM, etc. or a computer-readable signal 160 carrying the computer-readable instructions.

In the present example embodiment, the combination of the hardware components shown in FIG. 3, comprising the processor 120, the working memory 130 and the instruction store 140, is configured to implement the functionality of the control module 2 and the image data processing module 3, which will now be described in detail with reference to FIGS. 4 to 12.

Figure 4:
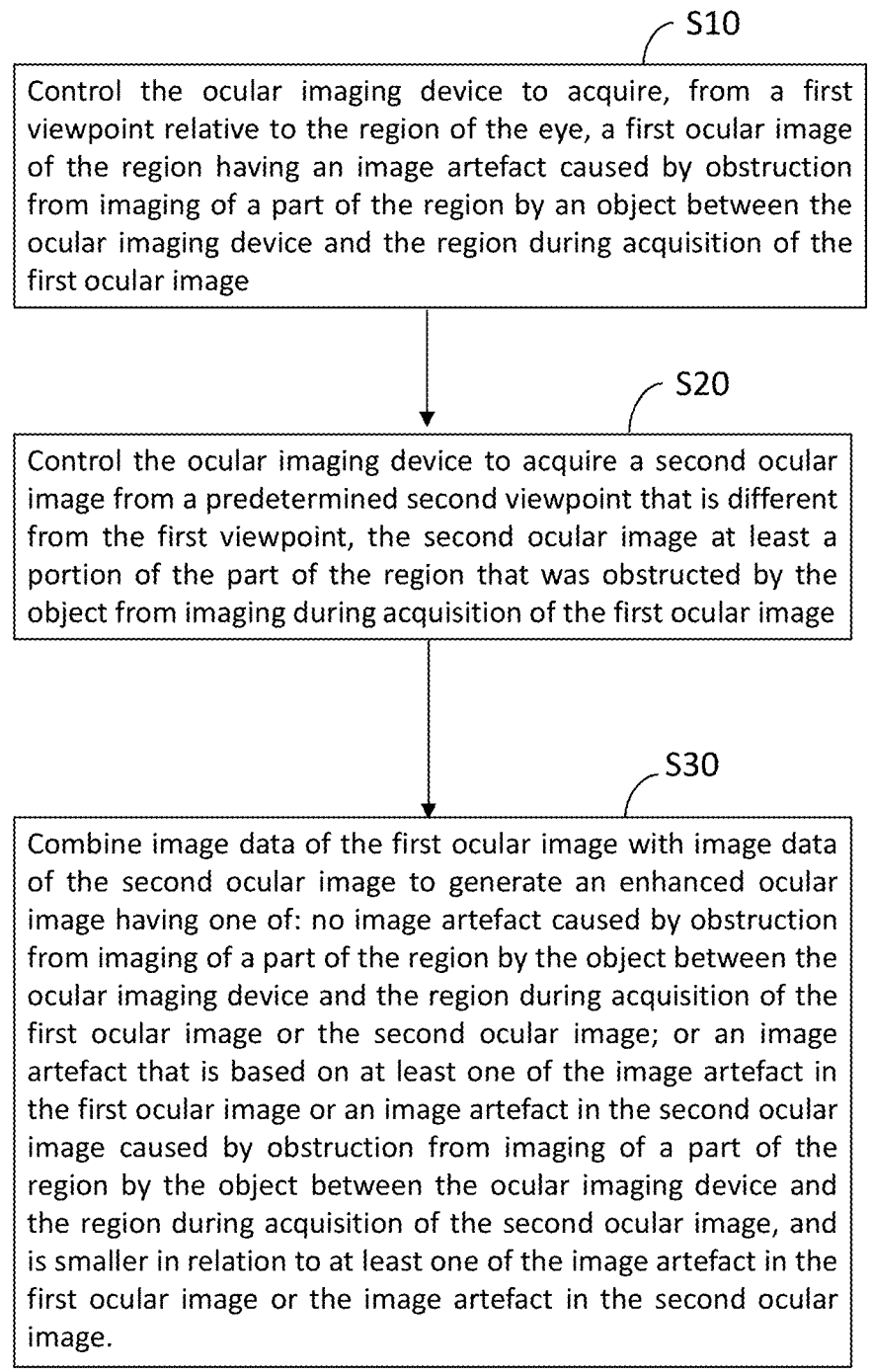
FIG. 4 shows a flow diagram of processes performed by the ophthalmic imaging system according to the first example embodiment herein.

FIG. 4 illustrates processes performed by the control module 2 and the image data processing module 3 according to the first example embodiment. In process S10 of FIG. 3, the control module 2 controls the ocular imaging device 1 to acquire the first ocular image 61 of the region 40 from the first viewpoint 60, the first ocular image 61 having the image artefact 62 illustrated in FIG. 2, which is caused by obstruction from imaging of a part of the region 40 by the object 50 between the ocular imaging device 1 and the region 40 during acquisition of the first ocular image 61.

In process S20 of FIG. 4 the control module 2 controls the ocular imaging device 1 to acquire the second ocular image 71 from the predetermined second viewpoint 70 that is different from the first viewpoint 60. The second ocular image 71 shows at least a portion of the part of the region 40 of the eye 80 that was obstructed by the object 50 from imaging during acquisition of the first ocular image 61.

In process S20 of FIG. 4, the control module 2 may, as in the present example embodiment, control the movement control module 4 to cause a predetermined movement of the viewpoint of the ocular imaging device 1 with respect to the region 40 of the eye 80, such that the ocular imaging device 1 is, following the predetermined movement, arranged to acquire the second ocular image 71 from the predetermined second viewpoint 70. Following the predetermined movement, the control module 2 controls the ocular imaging device 1 to acquire the second ocular image 71 of at least a part of the region 40 from the predetermined second viewpoint 70.

In process S30 of FIG. 4, the image data processing module 3 combines image data of the first ocular image 61 with the image data of the second ocular image 71 to generate an enhanced ocular image. The generated enhanced ocular image may have no image artefacts caused by obstruction from imaging of a part of the region 40 of the eye 80 by the object 50 during acquisition of the first ocular image 61 or the second ocular image 71. Alternatively, the enhanced ocular image may have an image artefact that is based on at least one of the image artefact in the first ocular image 61, or an image artefact in the second ocular image 71 that is caused by obstruction from imaging of a part of the region 40 of the eye 80 by the object 50 between the ocular imaging device 1 and the region 40 during acquisition of the second ocular image 71, and is smaller (e.g. in spatial extent and/or average pixel intensity) in relation to at least one of the image artefact in the first ocular image 61 or the image artefact in the second ocular image 71.

Figure 5A:
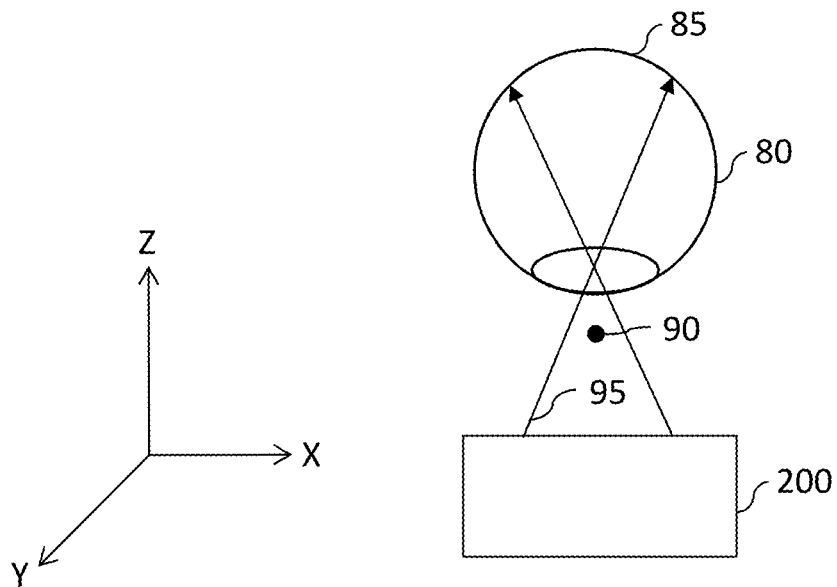
FIG. 5A illustrates an example of an SLO imaging device acquiring a first SLO image from a first viewpoint according to the first example embodiment herein.
Figure 5B:
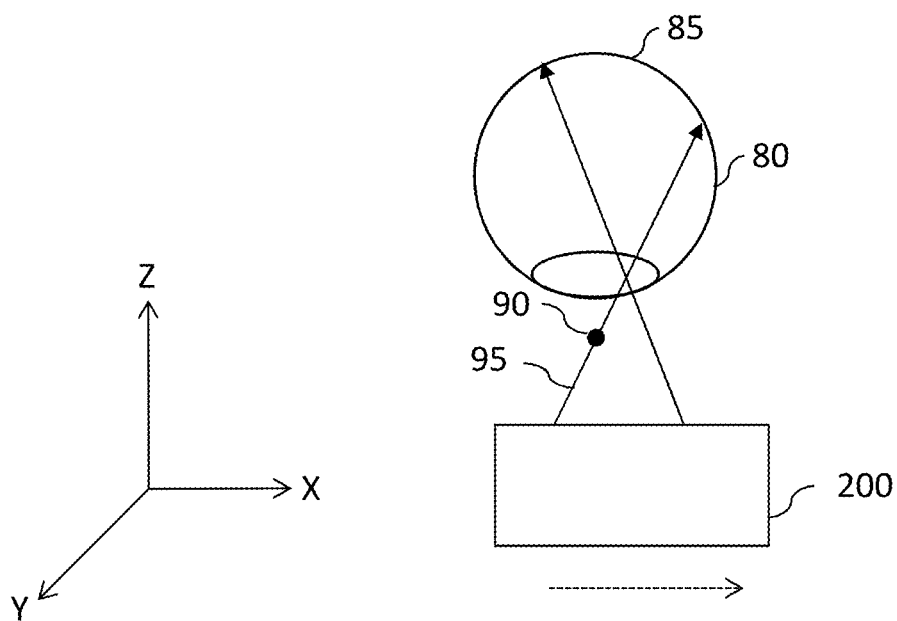
FIG. 5B illustrates the SLO imaging device in FIG. 5A acquiring a second SLO image from a predetermined second viewpoint according to the first example embodiment herein.

FIGS. 5A and 5B illustrate imaging operations performed by the ophthalmic imaging system 10 according to the first example embodiment. In the example of FIGS. 5A and 5B, the ophthalmic imaging device 1 is provided, by way of an example, in the form of an SLO imaging device 200. The SLO imaging device 200 is configured to produce an image of the retina 85 (as an example of the imaged region of the eye 80) by directing a laser beam 95, using horizontal and vertical scanning mirrors, over the retina 85 in a raster pattern, for example, and using a confocal filter and a light detector to detect the light reflected from each scanned point on the retina 85. The SLO imaging device 200 may employ an optical arrangement for wide-field imaging of the kind described in U.S. Pat. No. 5,815,242, for example, the contents of which are incorporated herein by reference in their entirety.

In the present example embodiment, the movement control module 4 comprises a movement mechanism 5, which is arranged to move the viewpoint of SLO imaging device 200 with respect to the eye 80 along at least one of three different movement axes. For convenience of explanation, the three movement axes are referred to as "X", "Y" and "Z" and are orthogonal, as illustrated in FIGS. 5A and 5B (although they need not be orthogonal in general). The form of the movement mechanism 5 is not limited and may, as in the present example embodiment, take the form of one or more stepper motors (not shown) that are arranged to move the SLO imaging device 200 along the respective movement axes using, e.g. a rack and pinion or other driving arrangement (not shown).

In FIG. 5A, the first viewpoint relative to the retina 85 is taken as a viewpoint of the SLO imaging device 200 relative to the retina 85 when the pupil of the eye 80 is laterally aligned with the focal point of the SLO imaging device 200, and when the eye 80 is positioned at a predetermined imaging distance from the SLO imaging device 200. An object in the form of an eyelash 90 obstructs a region of the retina 85 from being imaged by the SLO imaging device 200. After establishing alignment of the pupil with the focal point of the SLO imaging device 200 (which may be done using a pupil alignment module (PAM) of one of the many kinds well-known to those versed in the art), the SLO imaging device 200 is controlled by the control module 2 to capture a first SLO image from the first viewpoint by scanning the light beam 95 across a target region of interest on the retina 85, for example in a raster pattern. A photodetector in the SLO imaging device 200 (not shown) repeatedly detects the reflected light during the course of the scan, and the resulting image data is compiled by the SLO imaging device 200 to form the first SLO image.

Figure 8A:
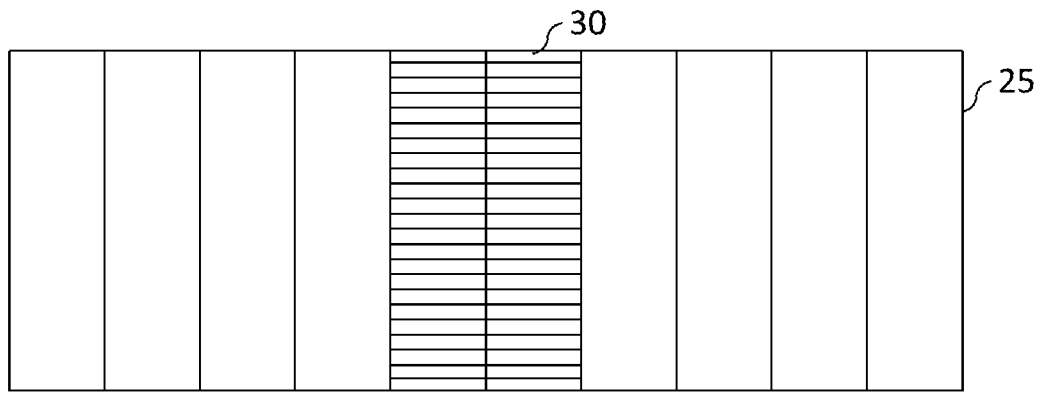
FIG. 8A illustrates a part of the first SLO image acquired from the first viewpoint illustrated in FIG. 5A.

FIG. 8A illustrates a section (slice) 25 of the first SLO image of the retina 85 captured by the SLO imaging device 200 from the first viewpoint illustrated in FIG. 5A. Due to the presence of the eyelash 90 preventing the SLO scan beam 95 from reaching a part of the retina 85, an image artefact 30 in the form of a shadowed area is formed on the first SLO image, reducing the amount of retinal information in the section of the first SLO image.

After acquiring the first SLO image, the control module 2 controls the movement control module 4 to make a predetermined movement of the viewpoint of the SLO imaging device 200 relative to the retina 85 along at least one of three different movement axes or by rotating the viewpoint of the SLO imaging device 200 about at least one of three different axes of rotation, in order to arrange the SLO imaging device 200 so that it can acquire the second ocular image 71 from the second predetermined viewpoint. As shown in FIG. 5B, the control module 2 controls the movement control module 4 to displace the SLO imaging device 200 by a predetermined distance along the X-axis to a predetermined second viewpoint relative to the retina 85, and then controls the SLO imaging device 200 to acquire the second SLO image from the predetermined second viewpoint.

Figure 8B:
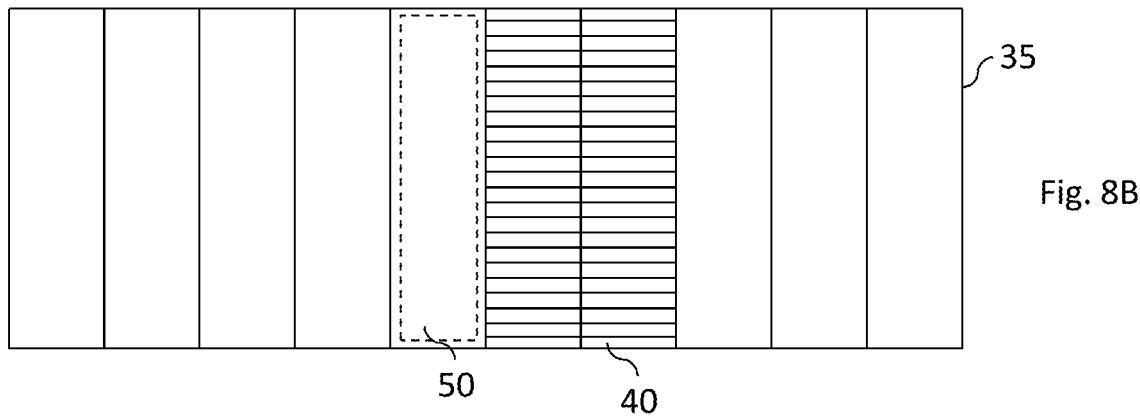
FIG. 8B illustrates a part of the second SLO image acquired from the second viewpoint illustrated in FIG. 5B.

FIG. 5B illustrates the SLO imaging device 200 to be displaced by a predetermined distance along the X-axis, so as to be arranged to image the eye 80 from the predetermined second viewpoint. From the second viewpoint, the SLO imaging device 200 again performs a raster scan or the like to acquire the second SLO image. FIG. 6B illustrates a section 35 of the corresponding second SLO image captured from the second viewpoint illustrated in FIG. 5B. Due to the parallax effect, during the capturing of the second SLO image, a part of the retina 85, which was blocked from imaging by the eyelash 90 when the first SLO image was captured, is successfully imaged from the predetermined second viewpoint. Accordingly, as shown in FIG. 8B, the corresponding section (slice) 35 of the second SLO image displays an image artefact 40 of substantially the same dimension as the image artefact 30 in the section 25 of the first SLO image but shifted to the right. By way of an example, the shift is by one pixel width in FIG. 8B. As region 50 of the second SLO image is covered by an image artefact 30 in the section 25 of the first SLO image (as illustrated in FIG. 8A), additional retinal content is provided by region 50 of the section 35 of the second SLO image.

It should be noted that any predetermined offset of the imaging viewpoint that allows the successful imaging of at least a part of the retina 85 that was previously blocked from imaging may be used. For example, in some example embodiments, the incident SLO scan beam 95 may be offset by a fraction of a pixel width to achieve sub-pixel size translation of the image artefact on the generated SLO image, for example.

Furthermore, although the present example embodiment employs bulk displacement of the SLO imaging device 200 to reach the predetermined second viewpoint of the SLO imaging device 200, in other example embodiments, instead of displacing the entire imaging device, the control module 2 may instead control one or more individual optical components of the SLO imaging 200 to be translated in a direction along one or more axes in the manner described above. The optical component may refer to any component of the SLO imaging device 200, such as a (e.g. elliptical) mirror or one or more lenses used to guide the SLO scan beam 95 onto the eye 80.

In some example embodiments, the viewpoint of the SLO imaging device 200 may be displaced along a plurality of axes to a plurality of further predetermined viewpoints and further SLO images can be captured from each of these viewpoints. For example, although FIG. 5B illustrates the displacement of the viewpoint of the SLO imaging device 200 along the X-axis, the viewpoint of the SLO imaging device 200 may additionally or alternatively be displaced along the Y-axis and/or Z-axis. Displacement of the viewpoint of the SLO imaging device 200 along the Z-axis, in a direction towards or away from the eye 80, would allow a varying amount of retinal content to be captured by the SLO imaging device 200. For example, by displacing the SLO imaging device 200 along the Z-axis to a position further away from the eye 80, a smaller part of the field of view of the SLO imaging device 200 would be occupied by the eyelash 90, allowing a larger area of the retina 85 to be imaged.

In some example embodiments, the control module 2 controls the movement control module 4 to cause a predetermined movement of one of the region 40 of the eye 80 and the viewpoint of the ocular imaging device 1 with respect to the other of the region 40 and the viewpoint of the ocular imaging device 1 in a movement direction along a predetermined axis that is based on an orientation of the image artefact in the first ocular image 61. More specifically, the predetermined movement of the ocular imaging device 1 may be performed in a movement direction that is substantially perpendicular to the orientation of the eyelash or other elongate object (e.g. a hair) which is located between the ocular imaging device 1 and the target region of interest on the eye 80. The orientation of the image artefact in the first ocular image 61 may be estimated using information indicative of the viewpoint of the ocular imaging device 1 relative to the eye 80. Alternatively, the orientation of the image artefact in the first ocular image 61 may be measured by detecting the orientation of an image artefact on the acquired ocular image. By using the orientation of the object 50 to select the direction of the predetermined movement, fewer images need to be acquired in order to effectively suppress the image artefact discussed herein.

Figures 6, 7:
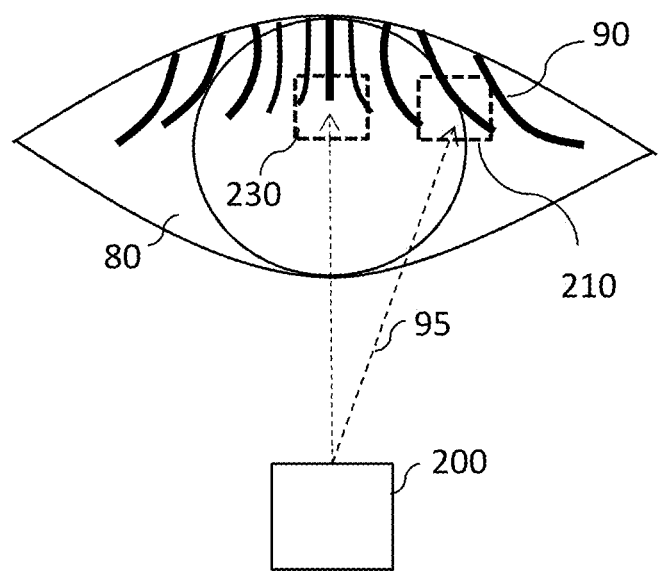
FIG. 6 illustrates the different orientation of eyelashes for two different viewpoints of the SLO imaging device.
FIG. 7 illustrates a mapping table for determining a required movement vector for moving the viewpoint of the SLO imaging device based on scan location.

As an example, in the first example embodiment, the predetermined movement of the viewpoint of the SLO imaging device 200 relative to the retina 85 is performed based on an estimated orientation of the eyelash 90. FIG. 6 illustrates an example of how the orientation of the eyelash 90 depends on the viewpoint of the SLO imaging device 200.

In FIG. 6, the SLO imaging device 200 is positioned relative to the eye 80 such that the pupil of the eye 80 is aligned with focal point of the SLO imaging device 200. From this position, when the SLO imaging device 200 is controlled to image a central region 230 of the retina 85, eyelash 90 in the field of view of the SLO imaging device 200 may appear substantially vertical, as illustrated in FIG. 6. In this scenario, a small horizontal displacement of the viewpoint of the SLO imaging device 200 may be sufficient to allow an area of the central region 230 previously covered by the eyelash 90 to be imaged.

However, as shown in FIG. 6, when the SLO scan beam 95 is directed to image a peripheral region 210 of the retina 85, for example, the orientation of the eyelash 90 may be slanted from the vertical direction in the acquired ocular images, or even appear substantially horizontal. Therefore, when imaging peripheral regions of the eye, movement of the viewpoint of SLO imaging device 200 along the vertical axis (Y-axis as shown in FIG. 5B) may be required to maximise the capture of retinal content.

Therefore, in the present example, the orientation of the eyelash 90 between the SLO imaging device 200 and a target scan region of the retina 85 may be estimated using target scan location information that is indicative of the location of the target scan region on the retina. The target scan location information may be provided, for example, in the form of an indication of respective orientations of the horizontal and vertical scanning mirrors which form part of the SLO imaging device 200, which orientations define a location on the retina about which the raster scan or the like is performed. As different scan regions on the retina 85 correspond to different sets of inclination angles for the horizontal and vertical scanning mirrors, the orientation of the eyelash 90 in the field of view of the SLO imaging device 200 may be estimated using the target scan location information and a mapping between scan regions on the retina and corresponding eyelash orientations, which mapping may be derived from examination of previously acquire ocular images, for example.

FIG. 7 illustrates an example of a look-up table which can be used to determine a movement direction of the viewpoint of the SLO imaging device 200 that is to be used for any given target scan region on the retina 85. In the look-up table of FIG. 7, a movement vector (v1 to v16) is stored for each pair of values that are indicative of scanning mirror inclination angles ($\theta$, $\varphi$), where angle $\theta$ is an inclination angle of the horizontal scanning mirror and angle $\varphi$ is an inclination angle of the vertical scanning mirror. Each movement vector defines a respective movement direction, and may further define a respective movement distance (although the movement distance may alternatively be predefined and independent of the movement direction). In the look-up table of FIG. 7, a respective movement vector is assigned to each pair of values indicative of the angles θ and θ), based on the estimated eyelash orientation for the specific region of the retina corresponding to that pair of values. The movement vector to be use for any planned scan region on the retina may be determined as the movement vector in the look-up table of FIG. 7 which corresponds to the pair of values indicative of scanning mirror angles θ and φ that are closest to those designating the planned scan region.

In some example embodiments, eyelash orientation may be measured or detected (rather than estimated) by applying an eyelash orientation detection algorithm to an acquired ocular image. For example, in some example embodiments, after acquiring the first ocular image 61 from the first viewpoint, the first ocular image 61 may first be processed to improve its contrast, using an algorithm such as Contrast Limited Adaptive Histogram Equalization (CLAHE). The contrast-enhanced first ocular image 61 may then be processed with a Gabor filter to determine the orientation of the eyelash 90 in the first ocular image 61. The parameters defining the size of the Gabor filter may be set to extract eyelashes from the image. The contrast-enhanced image may be processed with different versions of the Gabor filter set to different orientations. For each filtered image, binary thresholding may first be performed and the sum pixel intensity of the resulting image then calculated. The orientation of the Gabor filter which yields a filtered image with the highest sum pixel intensity after binary thresholding may be taken to indicate the orientation of the eyelash. Based on the measured eyelash orientation, the control module 2 may determine a movement direction along which to displace the ocular imaging device 1, in order to obtain a second viewpoint of the retina 85, for example by determining the movement direction to be perpendicular to the determined eyelash orientation. Thus, if the measured eyelash orientation is substantially horizontal, then a vertical displacement of the viewpoint of the ocular imaging device 1 may be applied by the control module 2. However, if the measured eyelash orientation is detected to be substantially vertical, then a horizontal displacement of the viewpoint may be applied by the control module 2.

The image data processing module 3 may, as in the present example embodiment, register the first and second ocular images with respect to each other, and generate the enhanced ocular image by averaging values of correspondingly located pixels in an area of overlap of the registered first and second ocular images. The image registration may, as in the present example embodiment, be performed by comparing the intensity values of the pixels in the two acquired SLO images using a correlation metric. However, the image registration may alternatively be performed based on image features such as a shape or contour corresponding to a particular part of the eye 80, for example blood vessels that are visible in retinal images.

For example, in FIG. 5B, the displacement of the viewpoint of the SLO imaging device 200 along the X-axis results in an offset in the area of the retina 85 being imaged, such that the retinal content of the first and second SLO images is not aligned. Therefore, before the SLO images can be combined to produce the enhanced SLO image, it may be preferable to register the first SLO image and the second SLO image with respect to each other.

Figure 9A:
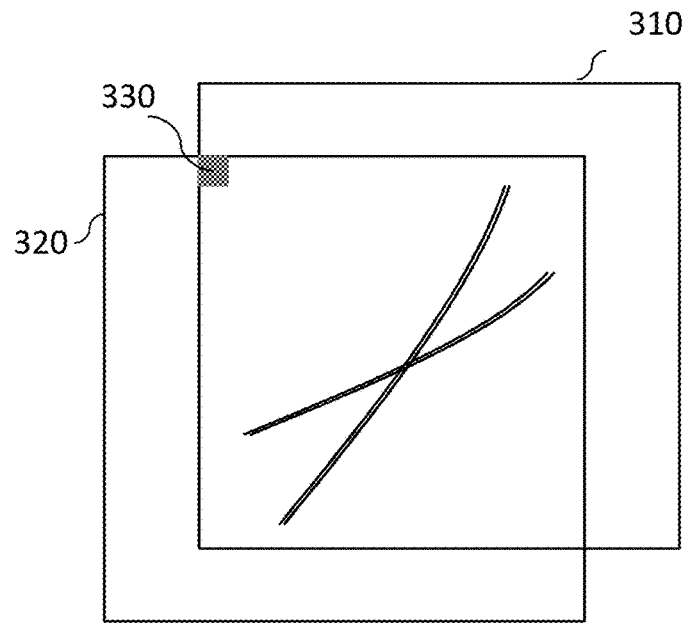
FIG. 9A illustrates a registration of two acquired SLO images.
Figure 9B:
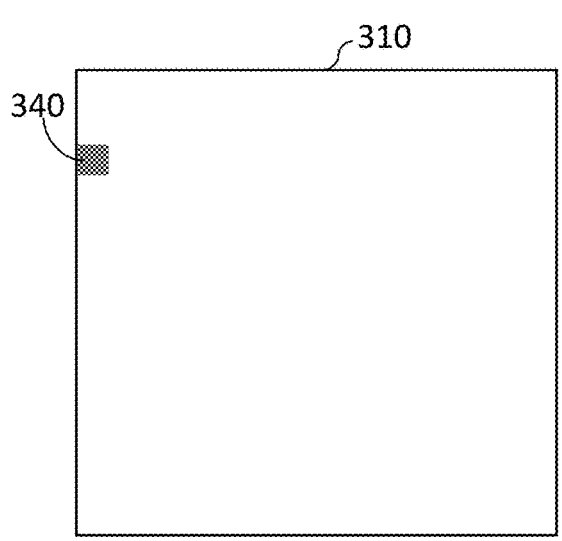
FIG. 9B illustrates a highlighted pixel in a first of the SLO images in FIG. 9A, which is used to generate a corresponding pixel of the enhanced SLO image.
Figure 9C:
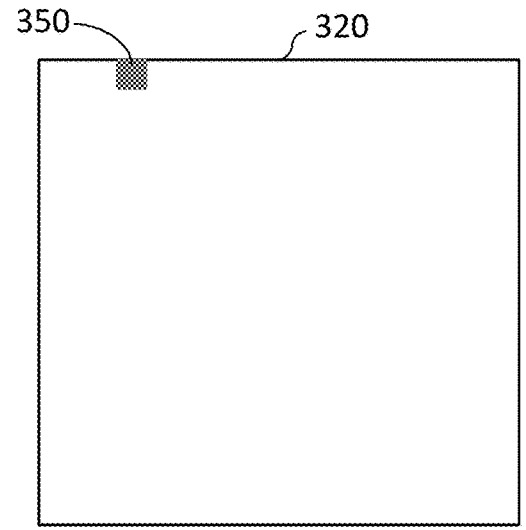
FIG. 9C illustrates a highlighted pixel in the second of the SLO images in FIG. 9A, which is correspondingly located to the highlighted pixel in FIG. 9B in the region of overlap between the registered first and second SLO images.

FIG. 9A illustrates an image registration process used in the present example embodiment, in which a two-dimensional cross-correlation of one SLO image with the other in order is calculated in order to determine a common area of lap in the first and second SLO images. In FIG. 9A, the first SLO image 310 is cross-correlated with the second SLO image 320 to align common eye content (e.g. retinal vasculature) in the two images. After the alignment, the common area of overlap between the two images represents the same region of the retina 85 that was commonly imaged in the two images. As an example, in FIGS. 9B and 9C, the highlighted pixel 340 in the first SLO image 310 and the highlighted pixel 350 in the second SLO image 320 correspond to the same region of the retina, based on the image alignment shown in FIG. 9A.

After registering the first SLO image 310 and the second SLO image 320 with respect to each other, an enhanced ocular image is generated by assigning, to each pixel of the enhanced ocular image, a pixel value obtained by averaging pixel values of correspondingly located pixels in the common area of overlap in the registered first and second ocular images. For example, in FIG. 9A, to form an enhanced ocular image of the region of overlap between the registered first and second SLO images, the pixel position 330 in the enhanced ocular image is formed by averaging the value of pixel 340 in the first SLO image 310 and the value of pixel 350 in the second SLO image 320 that are correspondingly located in the common area of overlap.

Figure 8C:
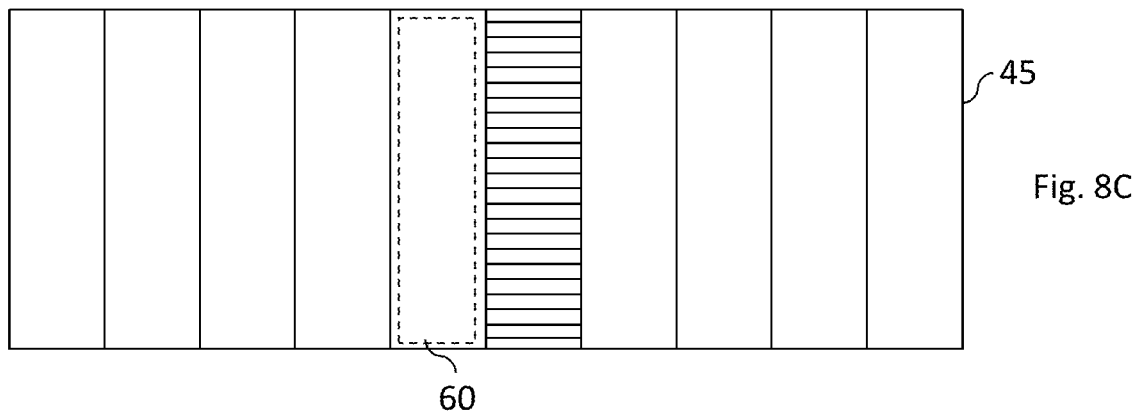
FIG. 8C illustrates a part of an enhanced SLO image generated from the parts of the first and second SLO images shown in FIGS. 6A and 6B, respectively.

FIG. 8C illustrates a section 45 of an enhanced image generated from the section 25 of the first SLO image and the section 35 of the second SLO image shown in FIGS. 8A and 8B, respectively, when pixel averaging as described above is used. Since the image artefacts 30, 40 of the first and second SLO images appear in the form of a shadow area, the section 45 of the enhanced image may display an image shadow artefact with a reduced darkness level compared to the image artefact at the corresponding pixel positions in the registered first or second SLO images. For example, in FIG. 8C, as a result of pixel averaging, region 60 of section 45 of the enhanced image displays an image artefact with reduced pixel intensity compared to the corresponding image region in section 25 of the first SLO image shown in FIG. 8A.

Although the present example uses two ocular images to generate the enhanced ocular image, it is possible to further improve the suppression of the image artefact by combining a larger of number of ocular images captured from different viewpoints relative to the eye 80. As long as an area of the eye blocked from imaging during the acquisition of one ocular image is visible in one or more further ocular images each taken from different viewpoints, the availability of the eye content in these further acquired images will contribute to the suppression the image artefact in the enhanced ocular image.

In some example embodiments, where the content of the first ocular image 61 and the second ocular image 71 is substantially aligned (i.e. when correspondingly located pixels in the first ocular image 61 and the second ocular image 71 represent the same location on the eye 80), image registration may not be required. Instead, the image data processing module 3 may directly generate the enhanced ocular image by calculating, as a respective pixel value of each pixel in the enhanced ocular image, a pixel value based on a sum of a pixel value of a respective pixel in the first ocular image 61 and a pixel value of a correspondingly located pixel in the second ocular image 71.

Although the aforementioned methods of generating an enhanced ocular image are based on pixel averaging, other image processing methods may alternatively be used to suppress the aforementioned image artefacts. Examples of such alternative image processing methods are set out below. It should be noted that the methods of generating the enhanced ocular image described below are not mutually exclusive, and may be combined to effectively suppress the image artefact in the enhanced image.

Figure 10:
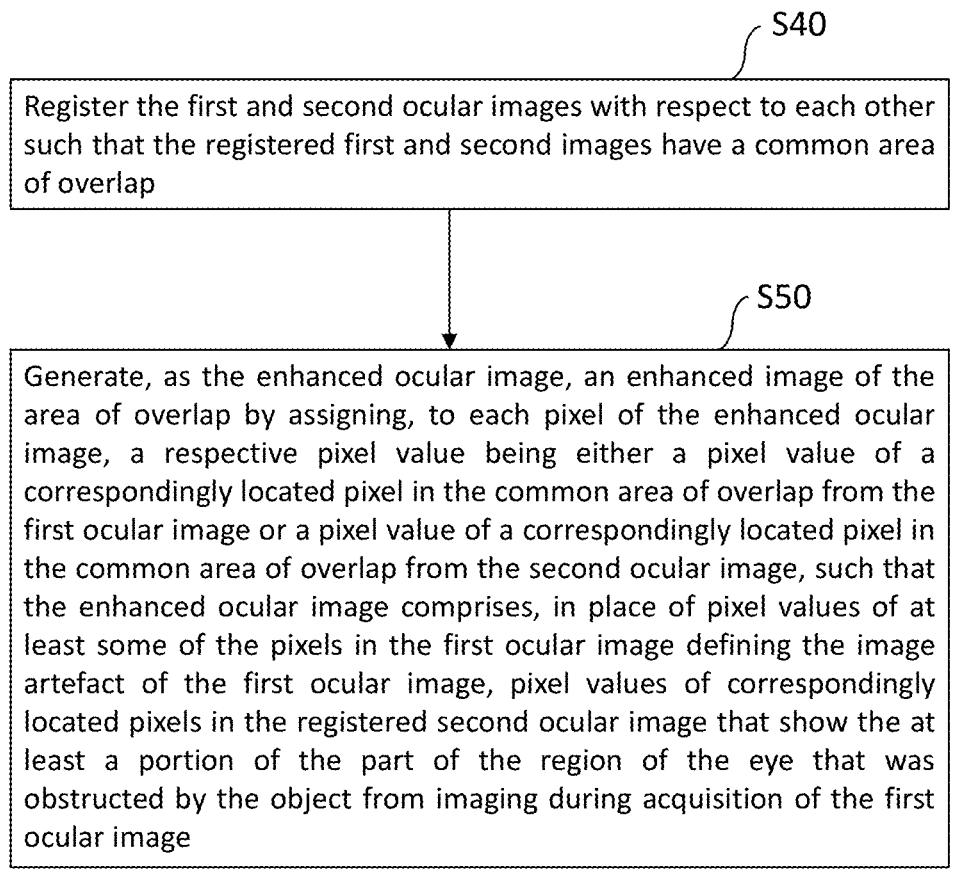
FIG. 10 illustrates a method of generating an enhanced ocular image with a reduced image artefact in the first example embodiment.

FIG. 10 illustrates an alternative method of generating an enhanced ocular image, which does not utilize pixel averaging.

At process S40 in FIG. 10, the image data processing module 3 registers the first ocular image 61 and the second ocular image 71 with respect to each other such that the registered first and second images have a common area of overlap.

The image data processing module 3 then generates, at process S50 of FIG. 10, as the enhanced ocular image, an enhanced image of the area of overlap by assigning, to each pixel of the enhanced ocular image, a respective pixel value being either a pixel value of a correspondingly located pixel in the common area of overlap from the first ocular image 61 or a pixel value of a correspondingly located pixel in the common area of overlap from the second ocular image 71. More specifically, the enhanced ocular image may comprise, in place of pixel values of at least some of the pixels in the first ocular image 61 defining the image artefact of the first ocular image 61, pixel values of correspondingly located pixels in the registered second ocular image that show the at least a portion of the part of the region 40 of the eye 80 that was obstructed by the object 50 from imaging during acquisition of the first ocular image 61. Alternatively, the enhanced ocular image may comprise, in place of pixel values of at least some of the pixels in the second ocular image defining the image artefact of the second ocular image 71, pixel values of correspondingly located pixels in the registered first ocular image that show at least a portion of the part of the region 40 that was obstructed by the object 50 from imaging during acquisition of the second ocular image 71.

To implement process S50, the image data processing module 3 may, as in the present example embodiment, classify each pixel in each of the first ocular image 61 and the second ocular image 71 as showing either an image of a corresponding part of the region of the eye or of the image artefact. For example, in the case of an image artefact caused by an eyelash 90 blocking SLO scan beam 95 from the SLO imaging device 200, the pixels forming the image artefact may be significantly darker than pixels representing retinal content. Therefore, the classification of pixels may comprise determining all pixels below a predetermined threshold to be pixels corresponding from an image artefact. The classification information may be stored in the form of a classification value for each pixel to indicate the pixel to either contain part of an image of the region of the eye or of an image artefact.

After performing classification for all the pixels in the registered first and second ocular images, the classification values for all correspondingly located pixels in a common area of overlap between the registered first and second ocular images are compared. The image data processing module 3 then creates the enhanced ocular image by generating the enhanced ocular image using pixels from the registered first and second ocular images. If a pixel in the common area of overlap of one of the registered first ocular image and the registered second ocular image is classified as showing part of an image of the region of the eye, and a correspondingly located pixel in the other of the registered first ocular image and registered second ocular image is classified as showing part of the image artefact, the pixel classified as showing part of the image of the region of the eye may be selected as the pixel to be assigned to the corresponding pixel location in the enhanced ocular image of the area of overlap between the registered first and second ocular images. If correspondingly located pixels in the common area of overlap of the registered first and second ocular images are both classified as showing part of the image of the region of the eye, then an average intensity of the corresponding two pixels can be computed and assigned to a corresponding pixel on the enhanced ocular image.

It should be noted that the enhanced ocular image may alternatively be generated by modifying one of the first ocular image 61 and the second ocular image 71. FIG. 11 illustrates a modification of the method in FIG. 10 where, after performing image registration at process S40 and pixel classification at process S60 as described above, the image data processing module 3 generates the enhanced ocular image, at process S70 of FIG. 11, by replacing pixel values of at least some of the pixels in the first ocular image 61 defining the image artefact of the first ocular image with 61 pixel values of correspondingly located pixels in the second ocular image 71 that show the at least a portion of the part of the region 40 of the eye 80 that was obstructed by the object 50 from imaging during acquisition of the first ocular image 61. The image data processing module 3 may alternatively replace pixel values of at least some of the pixels in the second ocular image 71 defining the image artefact of the second ocular image 71 with pixel values of correspondingly located pixels in the first ocular image 61 that show at least a portion of the part of the region 40 that was obstructed by the object 50 from imaging during acquisition of the second ocular image 71.

FIG. 12 illustrates an alternative method of generating an enhanced ocular image. In this alternative, the image data processing module 3 first performs image registration S40 and pixel classification S60 as described above with reference to FIG. 9. In process S80 of FIG. 12, the image data processing module 3 processes each of the first ocular image 61 and the second ocular image 71 to mask out the pixels showing the image artefact. The image data processing module 3 may, for example, perform the masking by setting the values of all the pixels in the first and second ocular images 61, 71 which are classified as showing part of the image artefact to zero. At process S90 in FIG. 12, the image data processing module 3 sums the pixel values of correspondingly located pixels in the resulting processed first ocular image and the resulting processed second ocular image to generate the enhanced image. The advantage of masking the pixels corresponding to the image artefact is that the output image would only contain eye content, so that image artefacts of the kind described above may be completely removed from the images.

In some example embodiments, after the pixel-wise classification value comparison is performed, if a significant number (i.e. a number above a predetermined threshold) of pixels in the common area of overlap are classified as image artefact in both the first ocular image 61 and the second ocular image 71, the control module 2 may control the ocular imaging device 1 to capture one or more further ocular images from different respective viewpoints relative the eye 80. In this scenario, the movement of the viewpoint of the ocular imaging device 1 to the further viewpoint(s) may be performed based on the location and/or distribution of the pixels in the common area of overlap which are classified as image artefact content in both the first ocular image 61 and the second ocular image 71.

Example Embodiment 2

In the first example embodiment, the control module 2 performs bulk movement of the ocular imaging device 1 relative to the eye 80 in at least one of three mutually perpendicular directions, in order to image the eye 80 from a different viewpoint. This type of displacement results in an offset in the scanned region of the eye 80. In the second example embodiment, however, the control module 2 is configured to control the ocular imaging device 1 to acquire images of substantially the same region 40 of the eye 80 from different viewpoints. In other respects, the present example embodiment is the same as the first example embodiment, and the variations and modifications to the first example embodiment described above are applicable to the present embodiment.

Figure 13:
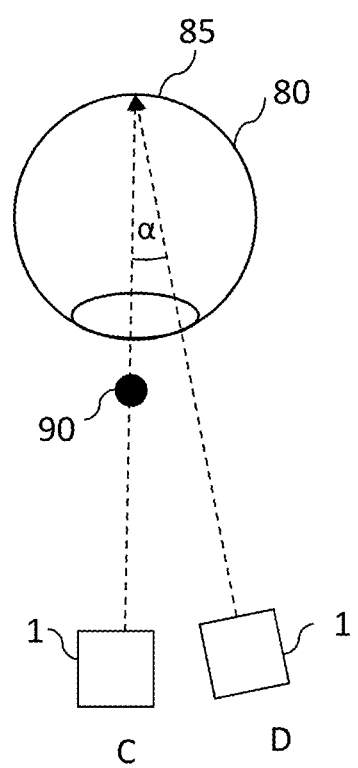
FIG. 13 illustrates an ocular imaging device acquiring a second ocular image from a second predetermined viewpoint according to a second example embodiment herein.

FIG. 13 illustrates an example of the second example embodiment, where a region of interest in the eye 80 is imaged from two different viewpoints. In the example of FIG. 13, a first ocular image 61 is taken from a first viewpoint labelled C, which is located along a first direction which is normal to the retina 85 of the eye 80 at a reference point in the imaged region of the retina 85. The control module 2 further displaces the ocular imaging device 1 to image the same region of interest from a second viewpoint, labelled D, which lies along a second direction that is at an angle α relative to the first direction at the reference point, as illustrated in FIG. 13. The displacement of the ocular imaging device 1 from viewpoint C to viewpoint D may be performed such that the distance between the reference point on the eye 80 and the ocular imaging device 1 is kept constant, for example by moving the ocular imaging device 1 along a predetermined arc around the eye 80 using the movement mechanism 5.

In the second example embodiment, the image data processing module 3 may generate the enhanced ocular image using any of the previously described methods. However, as the ocular images acquired from the first and second viewpoints are images of the same region of the eye taken from different angles, image registration does not need to be performed by the image data processing module 3.

Example Embodiment 3

A third example embodiment will now be described with reference to FIG. 14. In the present example embodiment, instead of causing a predetermined movement of the viewpoint of the ocular imaging device 1 with respect to the eye 80, the control module 2-1 illustrated in FIG. 14 controls the movement control module 4-1 to cause a predetermined movement of the region 40 of the eye 80 with respect to the viewpoint of the ocular imaging device 1, such that the ocular imaging device 1 is arranged to acquire the second ocular image from the predetermined second viewpoint. In other respects, the present example embodiment is the same as the first example embodiment, and the variations and modifications to the first example embodiment described above are applicable to the present embodiment.

Figure 14:
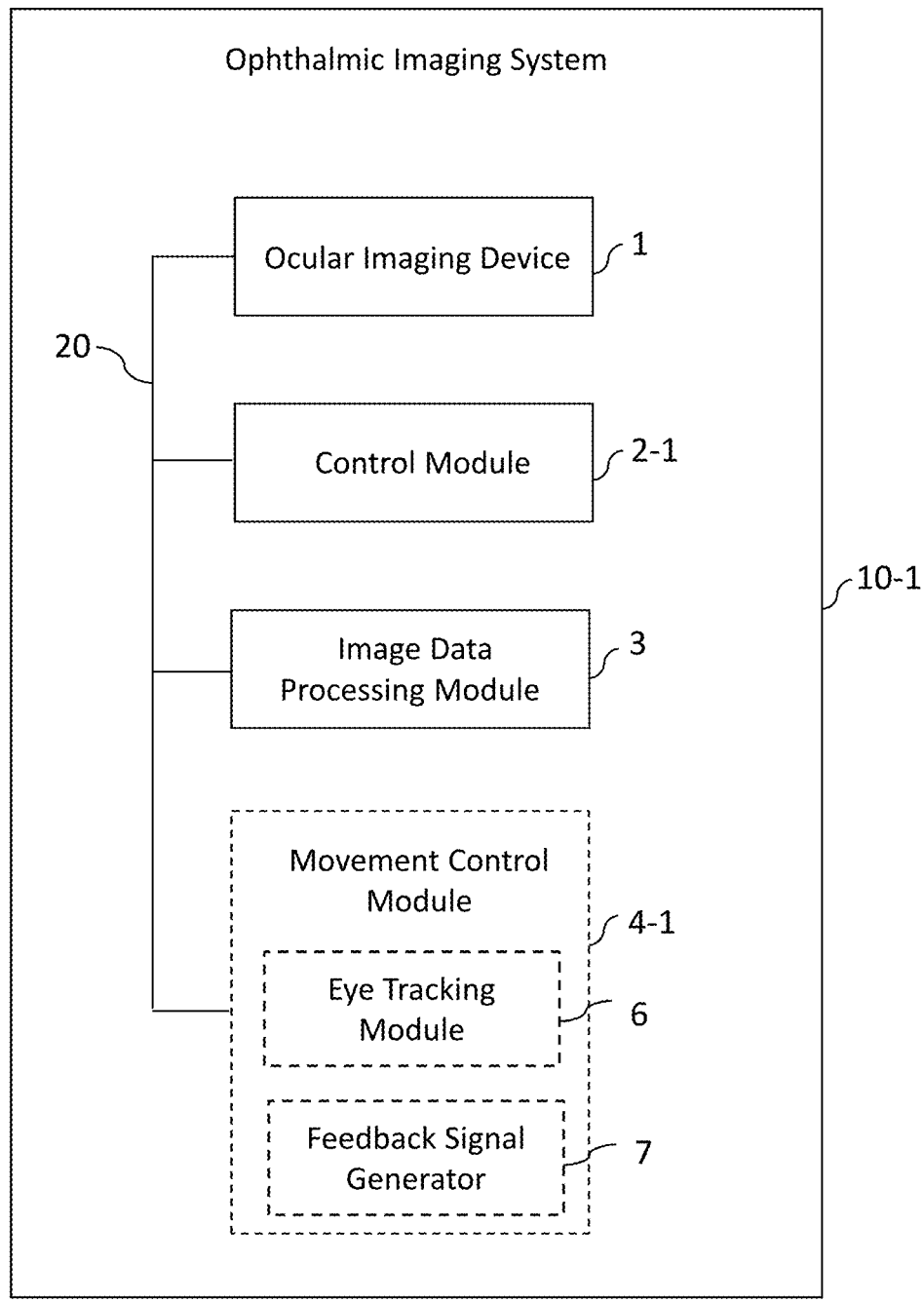
FIG. 14 is a schematic illustration of an ophthalmic imaging system according to a third example embodiment herein.

As illustrated in FIG. 14, the movement control module 4-1 comprises an eye tracking module 6, which is configured to monitor a position of the eye 80, and a feedback signal generator 7, which is configured to generate, based on the monitored position of the eye 80 and a predetermined target position of the eye 80, a feedback signal comprising a visual signal, an audio signal and/or a tactile signal (e.g. vibrations) for instructing the subject to move the eye 80 so that the monitored position of the eye 80 moves towards the target position of the eye 80. The control module 2-1 is configured to set the target position of the eye 80 such that the feedback signal generated by the feedback signal generator 7 guides the subject to make the predetermined movement of a region 40 of the eye 80 with respect to the ocular imaging device 1.

Accordingly, in the present example embodiment, a first ocular image is acquired from a first viewpoint of the ocular imaging device 1 as in the previous embodiments. After acquiring the first ocular image, the eye tracking module 6 may determine the current position of the eye 80 based on feature tracking and provide this positional information to the feedback signal generator 7. The feedback signal generator 7 may use the current position to determine an appropriate feedback signal to induce the required head movement from the subject so that the eye 80 is moved towards the target position. Once the subject has made the guided movement of the eye 80, the eye tracking module 6 may be used to confirm that the eye 80 is positioned at the target position, and a second ocular image can be captured. The acquired first and second ocular images may then be combined to generate the enhanced image using any of the previously described image data processing methods.

Example Embodiment 4

Figure 15:
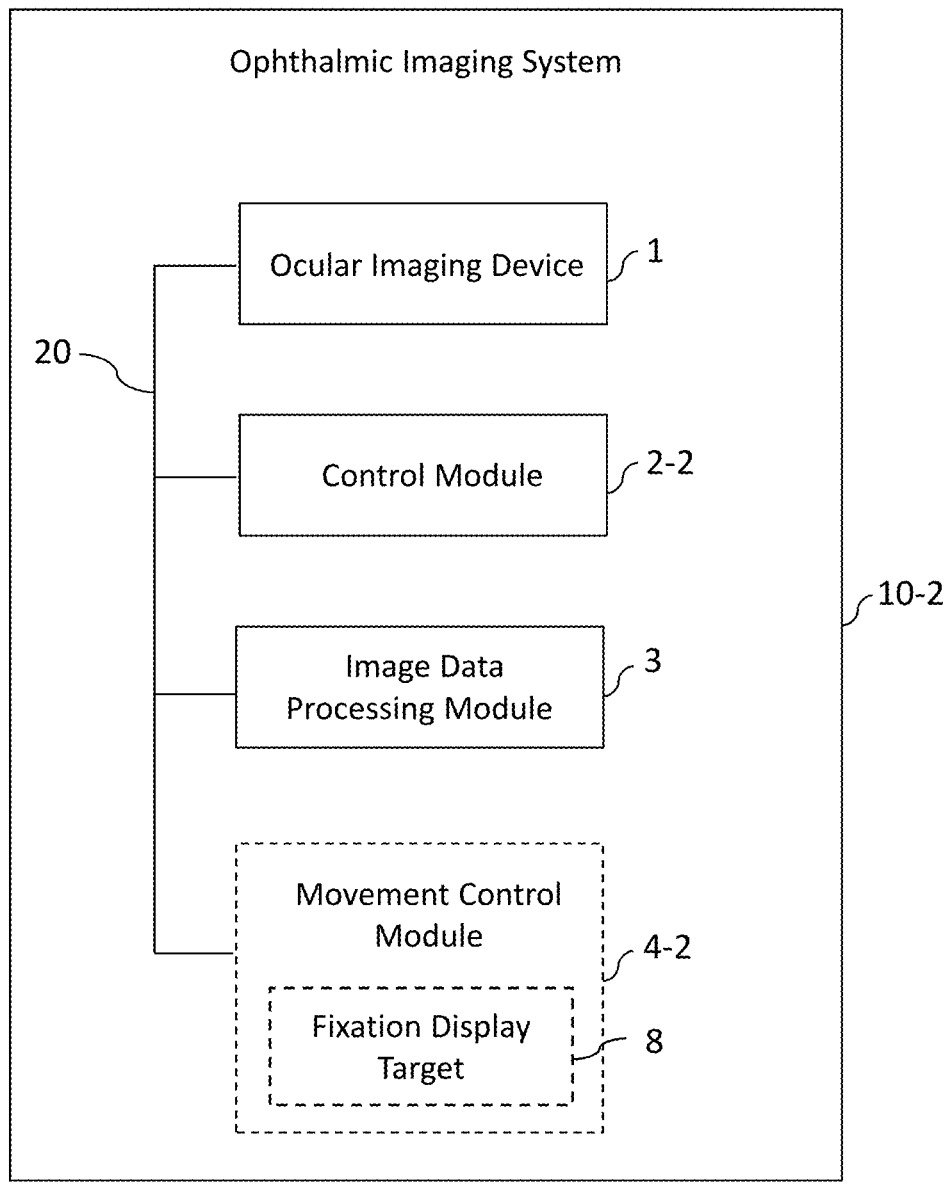
FIG. 15 is a schematic illustration of an ophthalmic imaging system according to a fourth example embodiment herein.

A fourth example embodiment will now be described with reference to FIGS. 15, 16A and 16B. In the present example embodiment, instead of causing bulk movement of the ocular imaging device 1 as described in the first example embodiment, or inducing bulk movement from the user as in the third example embodiment, the control module 2-2 is configured to cause the subject to change their gaze direction in order to obtain the second predetermined viewpoint relative to the region 40 of the eye 80, from which the second ocular image is to be captured. In other respects, the present example embodiment is the same as the first example embodiment, and the variations and modifications to the first example embodiment described above are applicable to the present embodiment.

In the present example embodiment, the movement control module 4-2 comprises a fixation target display 8, which is configured to display a fixation target 312 (FIGS. 16A and 16B) to the subject for setting a gaze direction 400 of the subject's eye 80. The control module 2-2 is configured to set a location of the displayed fixation target 312 in order to cause the predetermined change in the gaze direction 400 of the eye 80.

Figure 16A:
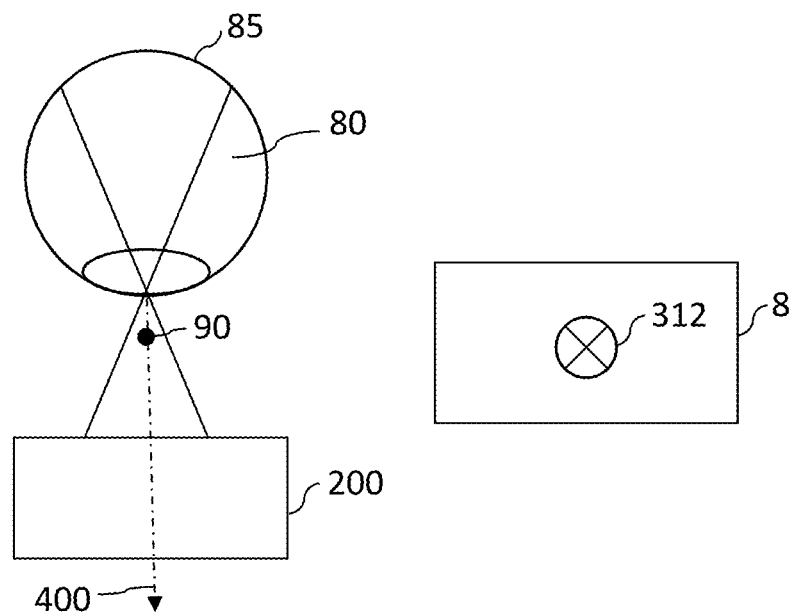
FIG. 16A is a schematic illustration of the ocular imaging device according to the fourth example embodiment acquiring a first ocular image from a first viewpoint relative to the eye.
Figure 16B:
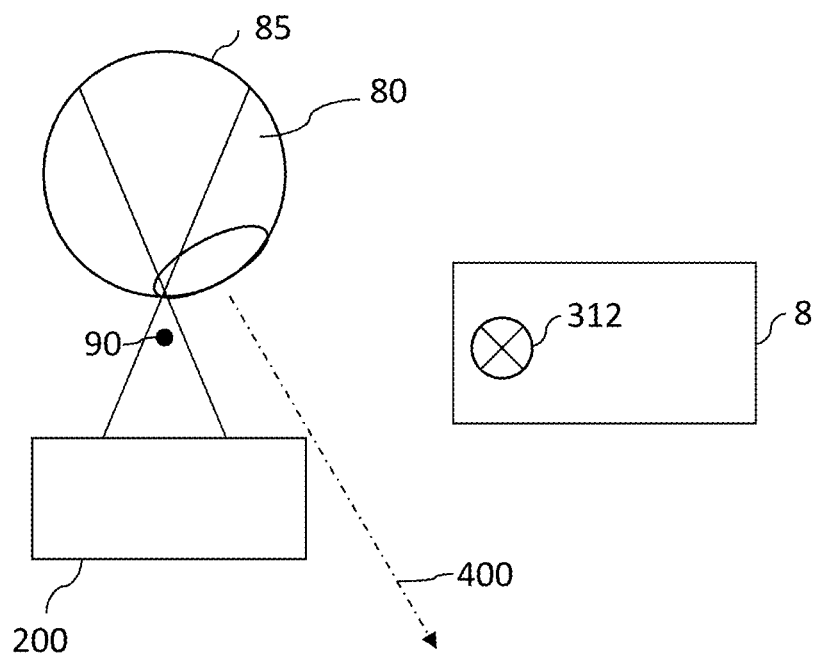
FIG. 16B is a schematic illustration of the ocular imaging device according to the fourth example embodiment acquiring a second ocular image from a predetermined second viewpoint relative to the eye.

FIGS. 16A and 16B provide further illustration of the fourth example embodiment. In FIG. 16A, a fixation target 312 is displayed in a central position on a fixation target display 8, for example, so that the subject looks straight towards the ocular imaging device 200. With the eye of the subject fixed on the fixation target 312, the ocular imaging device 1 acquires a first ocular image of the retina 85. Arrow 400 in FIG. 14A illustrates the gaze direction of eye 80 when the first ocular image is acquired.

In FIG. 16B, after the ocular imaging device 1 acquires the first ocular image, the fixation target 312 is subsequently displayed at a predetermined second position on the fixation target display 8, causing the subject to change their gaze direction. Accordingly, in FIG. 16B, the fixation target 312 is shown to have moved to the left side of the fixation target display 8, inducing the subject to direct their gaze towards the new fixation target position, in the direction illustrated by arrow 400. Once the gaze direction of the eye 80 has changed, the control module 2-2 controls the ocular imaging device 1 to acquire a second ocular image of the retina 85. By inducing a predetermined change in the gaze direction 400 of the eye 80 using a fixation target 312, a part of the eye 80 that was previously blocked from imaging by the eyelash 90 may be successfully imaged.

Example Embodiment 5

It should be noted that, in some example embodiments, the ophthalmic imaging system may be configured to acquire the first and second ocular image from the respective first and second viewpoints without requiring a relative movement of the eye 80 and the ocular imaging device 1. Instead, the ocular imaging device 1 may, as in the present example embodiment, comprise a first imaging apparatus provided at a first predetermined viewpoint relative to the eye 80, and a second imaging apparatus provided at a predetermined second viewpoint relative to the eye 80 which is different from the first viewpoint. The first imaging apparatus and the second imaging apparatus of the present example embodiment are controlled to acquire the first ocular image and the second ocular image, respectively, without any movement of the ophthalmic imaging system or the eye 80 being required. An enhanced ocular image may then be generated by the image data processing module 3 using any of the above-described methods. In other respects, the present example embodiment is the same as the first example embodiment, and the variations and modifications to the first example embodiment described above are applicable to the present example embodiment.

Example Embodiment 6

A sixth example embodiment will now be described with reference to FIGS. 17 to 21. In the example embodiments described above, a movement control module is employed to control a movement of either the eye or the viewpoint of the ocular imaging device, in order to acquire ocular images from different viewpoints and thus acquire information on the eye that could not be obtained from a single image, owing to the presence of an intervening eyelash or other object that obscures a part of the eye from imaging. The ophthalmic imaging system of the present example embodiment differs from the foregoing example embodiments in that it does not capture ocular images from different viewpoints but instead acquires images from a single viewpoint, employing a rotation of the ocular imaging device about a rotation axis passing through the eye and the viewpoint between the capture of the ocular images and an asymmetry of photodetector elements in a photodetector array of the ocular imaging device to effectively 'look around' the eyelash or other intervening object. The acquired ocular images are then combined to generate the enhanced image with reduced artefact presence, using any of the aforementioned methods performed by the image data processing module 3.

Figure 17:
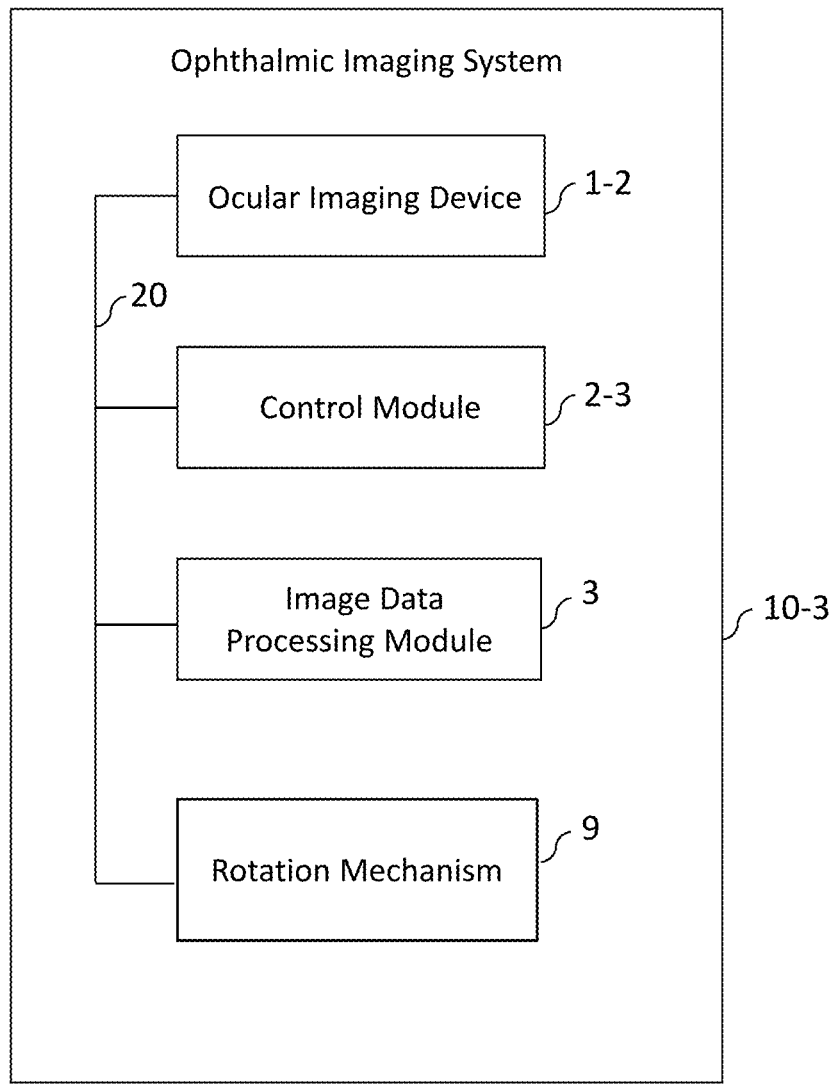
FIG. 17 illustrates an example of an ophthalmic imaging system according to a sixth example embodiment.
Figure 18:
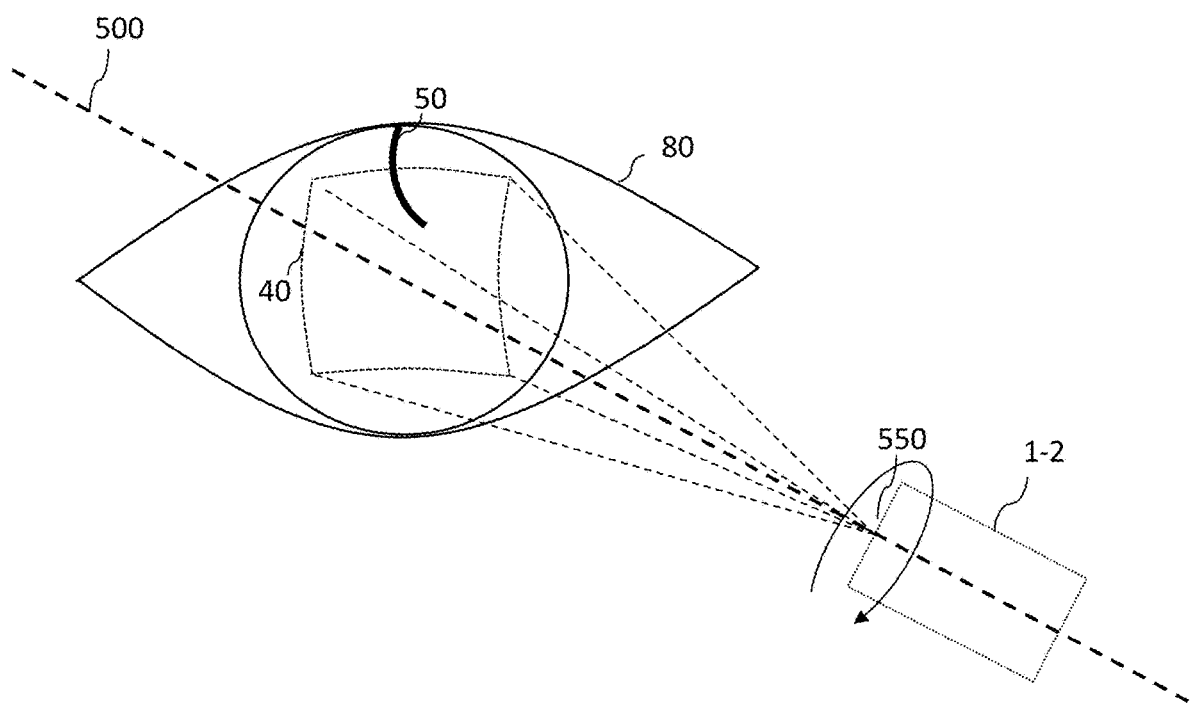
FIG. 18 illustrates a method of capturing a further ocular image from the same viewpoint after rotating the imaging device about an axis passing through the viewpoint of the ocular imaging device and the eye, according to the sixth example embodiment.
Figure 19:
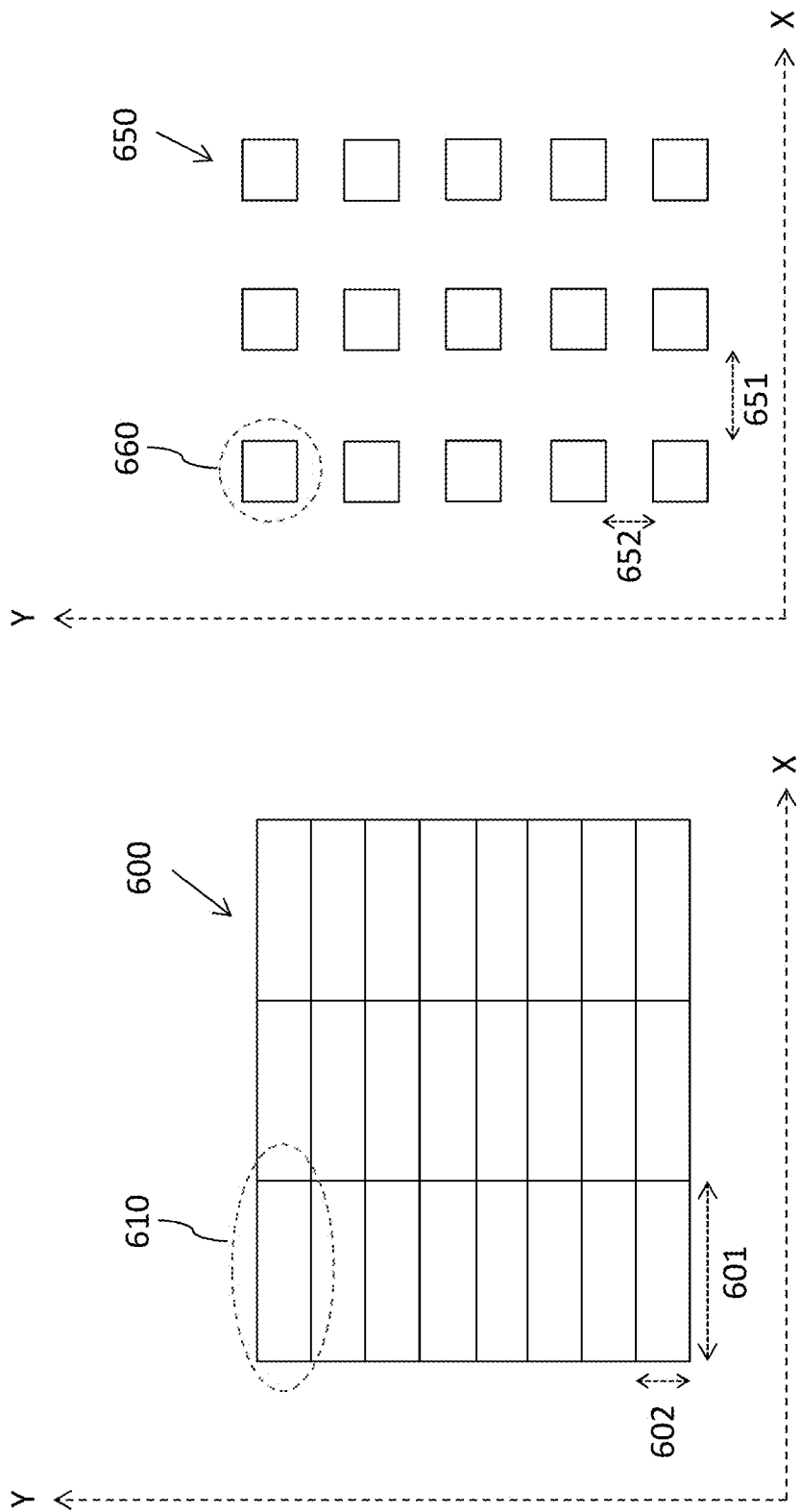
FIG. 19A illustrates a first example implementation of a two-dimensional array of photodetector elements for capturing an image of the eye.
FIG. 19B illustrates a second example implementation of a two-dimensional array of photodetector elements for capturing an image of the eye.

FIG. 17 illustrates an example of an ophthalmic imaging system 10-3 for generating an image of a region of an eye according to the sixth example embodiment. As illustrated in FIG. 17, the ophthalmic imaging system 10-3 comprises an ocular imaging device 1-2, a control module 2-3, an image data processing module 3 and a rotation mechanism 9. As illustrated in FIG. 18 and described in more detail below, after the ocular imaging device 1-2 has captured a first ocular image of a region 40 of the eye 80 from a viewpoint 550, the rotation mechanism 9 is controlled to rotate the ocular imaging device 1-2 by a predetermined angle about a rotation axis 500, which passes through the viewpoint 550 and the pupil or other part of the eye 80. After the rotation has been performed, the ocular imaging device 1-2 is controlled to capture a second ocular image from the same viewpoint 550. The predetermined angle may, as in the present embodiment, be $(2n+1)\pi/2$ radians, where n is an integer.

Referring now to FIGS. 19A and 19B, the ocular imaging device 1-2 comprises a two-dimensional array of photodetector elements operable to acquire an ocular image of the region 40. As shown in the example in FIG. 19A, each photodetector element 610 of the photodetector elements 600 may have a first length 601 along a first array direction (illustrated as X-direction) of the two-dimensional array 600 that differs from a second length 602 along a second array direction (illustrated as Y-direction) of the two-dimensional array 600. Alternatively or in addition, each photodetector element 660 of the photodetector elements 650 may, as shown by way of example in FIG. 19B, have a first separation 651 from a first adjacent photodetector element which is adjacent in the first array direction (illustrated X-direction), wherein the first separation 651 is different from a second separation 652 from a second adjacent photodetector element which is adjacent in the second array direction (illustrated as Y-direction in FIG. 19B).

The rotation mechanism 9 is configured to rotate the ocular imaging device 1-2 about the rotation axis 500 passing through the eye 80 and the viewpoint 550. The form of the rotation mechanism 9 is not limited and may, as in the present example embodiment, comprise a stepper motor arranged to rotate the ocular imaging device 1-2 about the rotation axis 500.

The control module 2-3 is configured to control the ocular imaging device 1-2 to acquire, from the viewpoint 550, a first ocular image of the region 40 having an image artefact caused by obstruction from imaging of a part of the region 40 by an object 50 between the ocular imaging device 1-2 and the region 40 during acquisition of the first ocular image.

The control module 2-3 is further configured to control the rotation mechanism 9 to rotate the ocular imaging device 1-2 about the rotation axis 500. Moreover, following the rotation of the ocular imaging device 1-2, the control module 2-3 is configured to control the ocular imaging device 1-2 to acquire a second ocular image from the (same) viewpoint 550, the second ocular image showing at least a portion of the part of the region 40 that was obstructed by the object 50 from being imaged during acquisition of the first ocular image.

The image data processing module 3 is configured as described above in relation to the first example embodiment, and may combine the first ocular image and the second ocular image to generate the enhanced image using any of the previously described image data processing methods. In particular, the image data processing module 3 is configured to combine image data of the first ocular image with image data of the second ocular image to generate an enhanced ocular image having one of: no image artefact caused by obstruction from imaging of a part of the region 40 by the object 50 between the ocular imaging device 1-2 and the region 40 during acquisition of the first ocular image or the second ocular image; or an image artefact that is based on at least one of the image artefact in the first ocular image, or an image artefact in the second ocular image caused by obstruction from imaging of a part of the region 40 by the object between the ocular imaging device 1-2 and the region 40 during acquisition of the second ocular image, and is smaller in relation to at least one of the image artefact in the first ocular image or the image artefact in the second ocular image.

As with the first example embodiment, the control module 2-3 and the image data processing module 3 of the sixth example embodiment may be implemented in programmable signal processing hardware, for example as described above with reference to FIG. 3.

Figure 20:
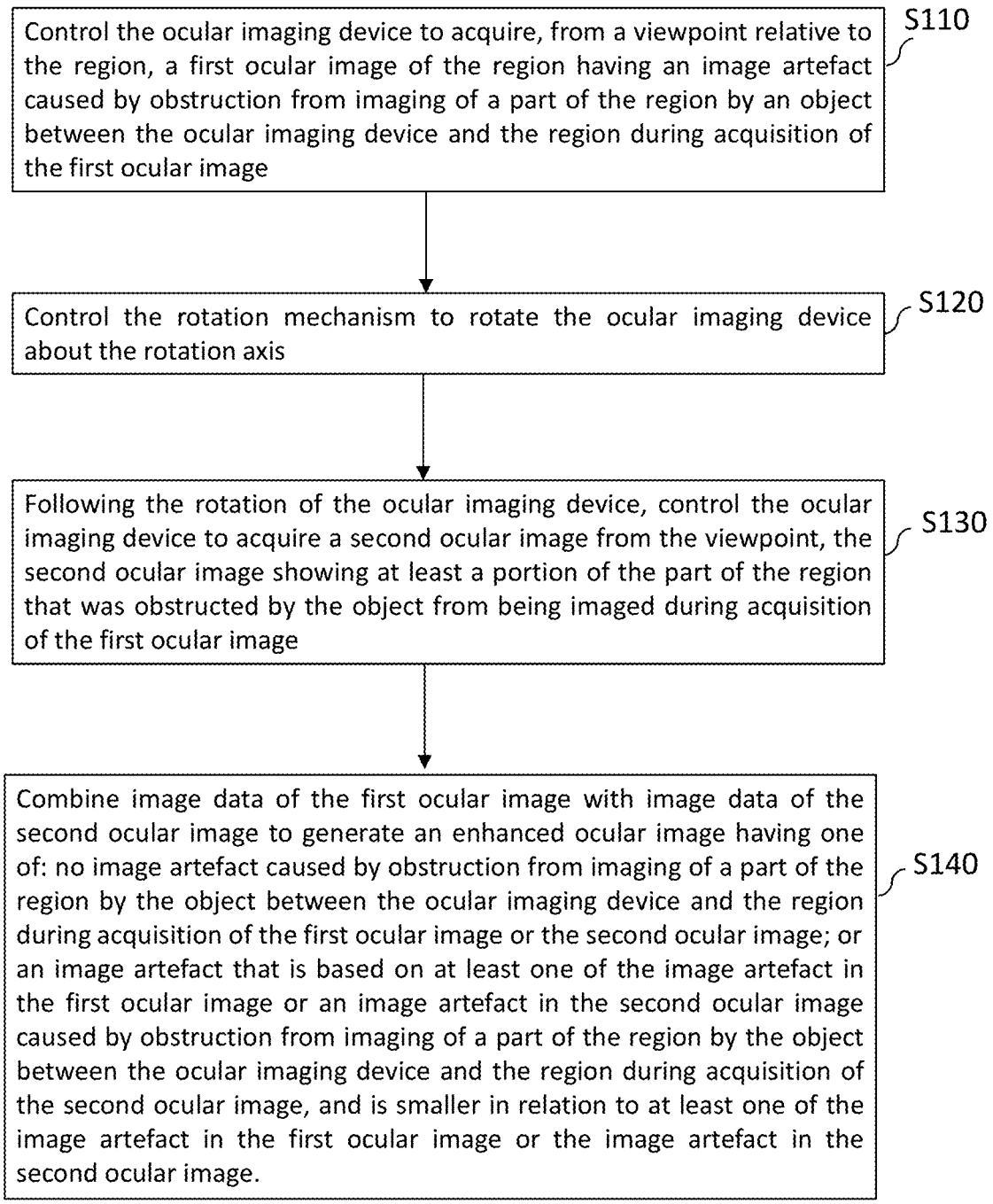
FIG. 20 is a flow diagram illustrating processes performed by the control module and the image data processing module according to the sixth example embodiment.

FIG. 20 illustrates processes performed by the control module 2-3 and the image data processing module 3 according to the sixth example embodiment. In process S110 of FIG. 20, the control module 2-3 controls the ocular imaging device 1-2 to acquire, from the viewpoint 550, a first ocular image of the region 40 having an image artefact which is caused by obstruction from imaging of a part of the region 40 by an object 50 between the ocular imaging device 1-2 and the region 40 during acquisition of the first ocular image.

In process S120 of FIG. 20, the control module 2-3 controls the rotation mechanism 9 to rotate the ocular imaging device 1-2 about the rotation axis 500 passing through the viewpoint 550 and the eye 80.

In process S130 of FIG. 20, following the rotation of the ocular imaging device 1-2, the control module 2-3 controls the ocular imaging device 1-2 to acquire a second ocular image from the viewpoint 550, the second ocular image showing at least a portion of the part of the region 40 that was obstructed by the object 50 from being imaged during acquisition of the first ocular image;

In process S140 of FIG. 20, the image data processing module 3 combines image data of the first ocular image with image data of the second ocular image to generate an enhanced ocular image having one of: no image artefact caused by obstruction from imaging of a part of the region 40 by the object 50 between the ocular imaging device 1-2 and the region 40 during acquisition of the first ocular image or the second ocular image; or an image artefact that is based on at least one of the image artefact in the first ocular image or an image artefact in the second ocular image caused by obstruction from imaging of a part of the region 40 by the object 50 between the ocular imaging device 1-2 and the region 40 during acquisition of the second ocular image, and is smaller in relation to at least one of the image artefact in the first ocular image or the image artefact in the second ocular image.

FIG. 21A provides an example illustration a photodetector array 810 of the ophthalmic imaging device 1-2 of the sixth example embodiment. As shown in FIG. 21A, the photodetector array 810 comprises a plurality of photodetector elements 812, where the width of each photodetector element 812 is greater than its height.

In FIG. 21A, during capture of the first ocular image by the photodetector array 810, light reflected from the eye 80 does not reach a region 814 of the photodetector array 810 as a result of an eyelash or other object 50 being in the field of view of the ocular imaging device 1-2. However, light reflected from the eye 80 is received by the other regions of the photodetector array 810. As shown in FIG. 21A, the light-blocked region 814 falls across the bottom five photodetector elements 812 located in the middle column of the photodetector array 810. The ocular image captured by the photodetector array 810, when the photodetector array 810 is illuminated with an illumination pattern as shown in FIG. 21A, is illustrated schematically in FIG. 21B. As shown in FIG. 21B, an image artefact 821 is formed in the ocular image 820. In the present example, it is assumed that light detected by each photodetector element in the photodetector array 810 is mapped to a correspondingly sized region of the generated ocular image and, therefore, the area of image artefact 821 is illustrated to correspond to the total area of the five photodetector array elements upon which the light-blocked region 814 falls. In other words, although the light-blocked region 814 covers only a portion of the area of each of the bottom five photodetector array elements in the middle column of photodetector array 810, all of the image pixels corresponding to each of the five photodetector elements are illustrated to be affected by the presence of the shadow in region 814, as shown in FIG. 21B.

After the ophthalmic imaging system 10-3 generates ocular image 820 based on the light received on the photodetector array in 810 as shown in FIG. 21A, the control module 2-3 controls the rotation mechanism 9 to rotate the ocular imaging device 1-2 clockwise by 90 degrees about the rotation axis 500 which passes through the eye 80 and the viewpoint 550. The ocular imaging device 1-2 is maintained at a same distance relative to the eye 80. Furthermore, the eye 80 and eyelash (or other object 50 blocking the eye 80) are both assumed to remain stationary while the ocular imaging device 1-2 is rotated.

FIG. 21C illustrates the illumination patter of light incident on the photodetector array 810 after the photodetector array 810 oriented as shown in FIG. 21A is rotated clockwise by 90 degrees. As shown in FIG. 21C, a light-blocked region 816 of the photodetector array 810 does not receive any light reflected from the eye 80 as a result of the eyelash or other object 50 being in the field of view of the ocular imaging device 1-2. As a result of the rotation, the light-blocked region 816 extends across only two of the photodetector array elements 812.

FIG. 21D illustrates the second ocular image 830, which is captured by the photodetector array 810 when the photodetector array 810 is orientated and illuminated with an illumination pattern as described above with reference to FIG. 21C. It should be noted that the photodetector element-to-pixel mapping used to map light intensity measurement values generated by the photodetector element values to respective ocular image pixels at this stage takes into account the rotation of the photodetector array 810, such that the ocular image 830 has the same orientation as ocular image 820. In FIG. 21D, an image artefact 822 is formed in the second ocular image 830 as a result of object 50 blocking light to region 816 of the photodetector array 810. Comparing ocular images 820 and 830, it is observed that artefact 821 of the first ocular image 820 extends over a larger portion of the ocular image than image artefact 822 in the second ocular image 830. However, the intensity of image artefact 822 of ocular image 830 is greater than the intensity of image artefact 821 in ocular image 820. This is because, in FIG. 21A, the region 814 deprived of the light reflected from the eye 80 only covers a small proportion of each of the photodetector elements that region 814 falls upon. In contrast, in FIG. 21C, light-blocked region 816 forms a significantly higher proportion of the area of the two photodetector elements upon which region 816 is overlaid in the example of FIG. 21C.

In this regard, it noted that ocular images 820 and 830 contribute different amount of retinal information and therefore can be combined by the image data processing module 3 to generate an enhanced image with reduced image artefact using any of the previously described methods. In particular, after obtaining images 820 and 830, the image data processing module 3 may be required to rotate one of the two images in order to ensure that the two images have the same orientation. The image data processing module 3 may register the two images against each other, and apply any of the image processing techniques described above to reduce the presence of image artefact in the final enhanced image. For example, the image data processing module may directly average ocular images 820 and 830, in order to reduce the intensity of image artefact 822 in ocular image 830. Alternatively, the image data processing module 3 may extract regions 823 of the ocular image 830 (as illustrated in FIG. 21D) which are not contaminated by any image artefact and use the extracted regions to "fill in" the corresponding areas of ocular image 820 which are corrupted by image artefact 821.

The example aspects described herein avoid limitations, specifically rooted in computer technology, relating to conventional techniques for conducting image scanning in optical scanning environments. In such conventional methods and systems, eyelashes and the like tend to obscure an image field of view, and can significantly reduce the amount of retinal content in an acquired image. The techniques of acquiring ocular images and combining the acquired ocular images described herein, on the other hand, can advantageously allow an enhanced ocular image to be created, in which image artefacts resulting from eyelashes and the like are reduced or eliminated altogether, allowing more of the imaged region of the eye to be visible in the image. By virtue thereof, imaging processing can be performed in a much less complex manner, and in a manner that requires relatively less computer processing and memory resources than those required by the conventional systems/methods, because the image artefacts can be detected and removed, thereby enabling imaging evaluations to be performed in a more highly computationally and resource-efficient manner relative to the conventional systems/methods. Also, by virtue of the foregoing capabilities of the example aspects described herein, which are rooted in computer technology, the example aspects described herein improve computers and computer processing/functionality, and also improve the field(s) of at least image processing, SLO, OCT, and data processing, and the processing of functional image data.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized (and navigated) in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment (and can form a memory or store). The program or instructions on the non-transitory machine-accessible medium, machine-readable medium, memory, instruction store, or computer-readable storage device or medium, may be used to program a computer system or other electronic device. The machine- or computer-readable device/medium, memory, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "com-puter-readable medium", "machine-accessible medium", "machine-readable medium", "memory", "instruction store", "computer-readable storage medium", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, memory, instruction store(s), or storage device(s), having instructions stored thereon or therein which can be used to control, or cause, a computer or computer processor to perform any of the procedures of the example embodiments described herein. The storage medium/memory/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, memory, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination. Having now described some illustrative embodiments and embodiments, it is apparent that the foregoing is illustrative and not limiting, having been presented by way of example.

The devices and apparatus described herein may be embodied in other specific forms without departing from the characteristics thereof. The foregoing embodiments are illustrative rather than limiting of the described systems and methods. Scope of the optical systems and apparatuses described herein is thus indicated by the appended claims, rather than the foregoing description, and changes that come within the meaning and range of equivalence of the claims are embraced therein.

The invention claimed is:

1. An ophthalmic imaging system for generating an image of a region of an eye of a subject, the ophthalmic imaging system comprising:
    an ocular imaging device operable to acquire an ocular image of the region;
    a control module configured to:
        control the ocular imaging device to acquire, from a first viewpoint relative to the region, a first ocular image of the region having an image artefact caused by obstruction from imaging of a part of the region by an object between the ocular imaging device and the region during acquisition of the first ocular image; and
        control the ocular imaging device to acquire a second ocular image from a predetermined second viewpoint that is different from the first viewpoint, the second ocular image showing at least a portion of the part of the region that was obstructed by the object from being imaged during acquisition of the first ocular image; and
    an image data processing module configured to combine image data of the first ocular image with image data of the second ocular image to generate an enhanced ocular image having one of:
        no image artefact caused by obstruction from imaging of a part of the region by the object between the ocular imaging device and the region during acquisition of the first ocular image or the second ocular image; or
        an image artefact that is based on at least one of the image artefact in the first ocular image, or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

2. The ophthalmic imaging system of claim 1, further comprising:
    a movement control module operable to control a movement of one of the region of the eye and a viewpoint of the ocular imaging device with respect to the other of the region and the viewpoint of the ocular imaging device,
    wherein the control module is configured to:
        control the movement control module to cause a predetermined movement of one of the region and the viewpoint of the ocular imaging device with respect to the other of the region and the viewpoint of the ocular imaging device such that the ocular imaging device is arranged to acquire the second ocular image from the predetermined second viewpoint; and
        following the predetermined movement, control the ocular imaging device to acquire the second ocular image from the predetermined second viewpoint.

3. The ophthalmic imaging system of claim 2, wherein the control module is configured to control the movement control module to cause, as the predetermined movement,
    a relative movement of the region of the eye and the viewpoint of the ocular imaging device caused by a predetermined change in a gaze direction of the eye.

4. The ophthalmic imaging system of claim 3, wherein the movement control module comprises a fixation target display configured to display a fixation target to the subject for setting a gaze direction of the eye, wherein the control module is configured to set a location of the displayed fixation target so as to cause the predetermined change in the gaze direction of the eye.

5. The ophthalmic imaging system of claim 2, wherein:
    the movement control module comprises a movement mechanism operable to make the predetermined movement by moving the viewpoint of the ocular imaging device with respect to the region along at least one of three different movement directions or by rotating the viewpoint of the ocular imaging device about at least one of three different axes of rotation; and
    the control module is configured to cause the movement control module to control the movement mechanism so as to make the predetermined movement.

6. The ophthalmic imaging system of claim 5, wherein the movement control module comprises:
    an eye tracking module configured to monitor a position of the eye; and
    a feedback signal generator configured to generate, based on the monitored position of the eye and a predetermined target position of the eye, a feedback signal comprising at least one of a visual signal, an audio signal and a tactile signal for instructing the subject to move the eye so that the monitored position of the eye moves towards the target position of the eye; and
    the control module is configured to set the target position of the eye such that the feedback signal generated by the feedback signal generator guides the subject to make the predetermined movement.

7. The ophthalmic imaging system of claim 2, wherein the control module is configured to control the movement control module to cause a predetermined movement of one of the region of the eye and the viewpoint of the ocular imaging device with respect to the other of the region and the viewpoint of the ocular imaging device in a movement direction that is based on an orientation of the image artefact in the first ocular image.

8. The ophthalmic imaging system of claim 1, wherein the image data processing module is configured to register the first and second ocular images with respect to each other, and to generate the enhanced ocular image by averaging values of correspondingly located pixels in an area of overlap of the registered first and second images.

9. The ophthalmic imaging system of claim 1, wherein the image data processing module is configured to:
 register the first and second ocular images with respect to each other such that the registered first and second images have a common area of overlap; and
 generate, as the enhanced ocular image, an enhanced image of the area of overlap by assigning, to each pixel of the enhanced ocular image, a respective pixel value being either a pixel value of a correspondingly located pixel in the common area of overlap from the first ocular image or a pixel value of a correspondingly located pixel in the common area of overlap from the second ocular image, such that:
  the enhanced ocular image comprises, in place of pixel values of at least some of the pixels in the first ocular image defining the image artefact of the first ocular image, pixel values of correspondingly located pixels in the registered second ocular image that show the at least a portion of the part of the region of the eye that was obstructed by the object from imaging during acquisition of the first ocular image; or
  the enhanced ocular image comprises, in place of pixel values of at least some of the pixels in the second ocular image defining the image artefact of the second ocular image, pixel values of correspondingly located pixels in the registered first ocular image that show at least a portion of the part of the region that was obstructed by the object from imaging during acquisition of the second ocular image.

10. The ophthalmic imaging system of claim 1, wherein the image data processing module is configured to generate the enhanced ocular image by:
 classifying each pixel in each of the first ocular image and the second ocular image as showing either a respective part the eye or a respective part of the image artefact;
 processing each of the first ocular image and the second ocular image to mask out pixels showing the image artefact; and
 summing pixel values of correspondingly located pixels in the processed first ocular image and the second ocular image.

11. The ophthalmic imaging system according to claim 1, wherein the ocular imaging device comprises at least one of a scanning laser ophthalmoscope or an optical coherence tomography imaging system.

12. The ophthalmic imaging system according to claim 1, wherein the object is one of a hair, an eyelash of the eye, an iris of the eye and an eyelid of the eye.

13. An ophthalmic imaging system for generating an image of a region of an eye of a subject, the ophthalmic imaging system comprising:
 an ocular imaging device comprising a two-dimensional array of photodetector elements and operable to acquire an ocular image of the region from a viewpoint, wherein each photodetector element of the photodetector elements has at least one of:
  a first length along a first array direction of the two-dimensional array that differs from a second length along a second array direction of the two-dimensional array; or
  a first separation from a first adjacent photodetector element which is adjacent in the first array direction, the first separation being different from a second separation of the photodetector element from a second adjacent photodetector element which is adjacent in the second array direction;
 a rotation mechanism configured to rotate the ocular imaging device about a rotation axis passing through the eye and the viewpoint;
 a control module configured to:
  control the ocular imaging device to acquire, from the viewpoint, a first ocular image of the region having an image artefact caused by obstruction from imaging of a part of the region by an object between the ocular imaging device and the region during acquisition of the first ocular image;
  control the rotation mechanism to rotate the ocular imaging device about the rotation axis; and
  following the rotation of the ocular imaging device, control the ocular imaging device to acquire a second ocular image from the viewpoint, the second ocular image showing at least a portion of the part of the region that was obstructed by the object from being imaged during acquisition of the first ocular image; and
 an image data processing module configured to combine image data of the first ocular image with image data of the second ocular image to generate an enhanced ocular image having one of:
  no image artefact caused by obstruction from imaging of a part of the region by the object between the ocular imaging device and the region during acquisition of the first ocular image or the second ocular image; or
  an image artefact that is based on at least one of the image artefact in the first ocular image, or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

14. A computer-readable storage device comprising instructions that, when executed by a processor, cause the processor to perform a set of operations to control an ophthalmic imaging system comprising an ocular imaging device operable to acquire an image of a region of an eye of a subject, the set of operations comprising:
 controlling the ocular imaging device to acquire, from a first viewpoint relative to the region, a first ocular image of the region having an image artefact caused by obstruction from imaging of a part of the region by an object between the ocular imaging device and the region during acquisition of the first ocular image;
 controlling the ocular imaging device to acquire a second ocular image from a predetermined second viewpoint that is different from the first viewpoint, the second ocular image showing at least a portion of the part of the region that was obstructed by the object from being imaged during acquisition of the first ocular image; and combining image data of the first ocular image with image data of the second ocular image to generate an enhanced ocular image having one of:
  no image artefact caused by obstruction from imaging of a part of the region by the object between the ocular imaging device and the region during acquisition of the first ocular image or the second ocular image; or
  an image artefact that is based on at least one of the image artefact in the first ocular image or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

15. The computer-readable storage device of claim 14, wherein the set of operations further comprises:
  registering the first and second ocular images with respect to each other; and
  generating the enhanced ocular image by averaging values of correspondingly located pixels in an area of overlap of the registered first and second images.

16. The computer-readable storage device of claim 14, wherein the set of operations further comprises:
  registering the first and second ocular images with respect to each other such that the registered first and second images have a common area of overlap; and
  generating, as the enhanced ocular image, an enhanced image of the area of overlap by assigning, to each pixel of the enhanced ocular image, a respective pixel value being either a pixel value of a correspondingly located pixel in the common area of overlap from the first ocular image or a pixel value of a correspondingly located pixel in the common area of overlap from the second ocular image, such that:
    the enhanced ocular image comprises, in place of pixel values of at least some of the pixels in the first ocular image defining the image artefact of the first ocular image, pixel values of correspondingly located pixels in the registered second ocular image that show the at least a portion of the part of the region of the eye that was obstructed by the object from imaging during acquisition of the first ocular image; or
    the enhanced ocular image comprises, in place of pixel values of at least some of the pixels in the second ocular image defining the image artefact of the second ocular image, pixel values of correspondingly located pixels in the registered first ocular image that show at least a portion of the part of the region that was obstructed by the object from imaging during acquisition of the second ocular image.

17. The computer-readable storage device of claim 14, wherein the set of operations further comprises:
  classifying each pixel in each of the first ocular image and the second ocular image as showing either a respective part the eye or a respective part of the image artefact;
  processing each of the first ocular image and the second ocular image to mask out pixels showing the image artefact; and
  summing pixel values of correspondingly located pixels in the processed first ocular image and the second ocular image.

18. The computer-readable storage device of claim 14, wherein the ocular imaging device comprises at least one of a scanning laser ophthalmoscope or an optical coherence tomography imaging system.

19. The computer-readable storage device of claim 14, wherein the object is one of a hair, an eyelash of the eye, an iris of the eye and an eyelid of the eye.

20. A computer program comprising instructions which, when the computer program is executed by a processor, cause the processor to control an ophthalmic imaging system comprising:
  an ocular imaging device comprising a two-dimensional array of photodetector elements and operable to acquire an ocular image of the region from a viewpoint, wherein each photodetector element of the photodetector elements has at least one of:
    a first length along a first array direction of the two-dimensional array that differs from a second length along a second array direction of the two-dimensional array; or
    a first separation from a first adjacent photodetector element which is adjacent in the first array direction, the first separation being different from a second separation of the photodetector element from a second adjacent photodetector element which is adjacent in the second array direction; and
  a rotation mechanism configured to rotate the ocular imaging device about a rotation axis passing through the eye and the viewpoint,
  wherein the instructions, when the computer program is executed by a processor, cause the processor to control the ophthalmic imaging system by:
    controlling the ocular imaging device to acquire, from the viewpoint, a first ocular image of the region having an image artefact caused by obstruction from imaging of a part of the region by an object between the ocular imaging device and the region during acquisition of the first ocular image;
    controlling the rotation mechanism to rotate the ocular imaging device about the rotation axis; and
    following the rotation of the ocular imaging device, controlling the ocular imaging device to acquire a second ocular image from the viewpoint, the second ocular image showing at least a portion of the part of the region that was obstructed by the object from being imaged during acquisition of the first ocular image; and
    combining image data of the first ocular image with image data of the second ocular image to generate an enhanced ocular image having one of:
      no image artefact caused by obstruction from imaging of a part of the region by the object between the ocular imaging device and the region during acquisition of the first ocular image or the second ocular image; or
      an image artefact that is based on at least one of the image artefact in the first ocular image or an image artefact in the second ocular image caused by obstruction from imaging of a part of the region by the object between the ocular imaging device and the region during acquisition of the second ocular image, and is smaller in relation to at least one of the image artefact in the first ocular image or the image artefact in the second ocular image.

* * * * *